United States Patent
Vizcardo et al.

(10) Patent No.: US 12,037,607 B2
(45) Date of Patent: Jul. 16, 2024

(54) METHODS OF PREPARING HEMATOPOIETIC PROGENITOR CELLS IN VITRO

(71) Applicant: The United States of America, as represented by the Secretary, Department of Health and Human Services, Bethesda, MD (US)

(72) Inventors: Raul E. Vizcardo, Foster City, CA (US); Naritaka Tamaoki, North Bethesda, MD (US); Meghan L. Good, Derwood, MD (US); Nicholas P. Restifo, Chevy Chase, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 787 days.

(21) Appl. No.: 16/762,447

(22) PCT Filed: Nov. 8, 2018

(86) PCT No.: PCT/US2018/059856
§ 371 (c)(1),
(2) Date: May 7, 2020

(87) PCT Pub. No.: WO2019/094614
PCT Pub. Date: May 16, 2019

(65) Prior Publication Data
US 2020/0263136 A1    Aug. 20, 2020

Related U.S. Application Data

(60) Provisional application No. 62/583,240, filed on Nov. 8, 2017.

(51) Int. Cl.
*C12N 5/0789* (2010.01)
*A61K 35/28* (2015.01)

(52) U.S. Cl.
CPC ............ *C12N 5/0647* (2013.01); *A61K 35/28* (2013.01); *C12N 2500/98* (2013.01); *C12N 2501/115* (2013.01); *C12N 2501/125* (2013.01); *C12N 2501/135* (2013.01); *C12N 2501/145* (2013.01); *C12N 2501/155* (2013.01); *C12N 2501/165* (2013.01); *C12N 2501/20* (2013.01); *C12N 2501/22* (2013.01); *C12N 2501/2303* (2013.01); *C12N 2501/2306* (2013.01); *C12N 2501/24* (2013.01); *C12N 2501/25* (2013.01); *C12N 2501/415* (2013.01); *C12N 2502/00* (2013.01); *C12N 2506/45* (2013.01); *C12N 2513/00* (2013.01); *C12N 2531/00* (2013.01)

(58) Field of Classification Search
None
See application file for complete search history.

(56) References Cited

U.S. PATENT DOCUMENTS

| 7,575,925 B2 | 8/2009 | Schmitt et al. |
| 2014/0273211 A1 | 9/2014 | Slukvin et al. |

FOREIGN PATENT DOCUMENTS

| EP | 2 615 165 A1 | 7/2013 |
| WO | WO 2017/096215 A1 | 6/2017 |
| WO | WO 2018/067836 A1 | 4/2018 |

OTHER PUBLICATIONS

Choi et al. "Hematopoietic and endothelial differentiation of human induced pluripotent stem cells." Stem Cells 27.3 (2009): 559-567. (Year: 2009).*
Dang et al. "Efficiency of embryoid body formation and hematopoietic development from embryonic stem cells in different culture systems." Biotechnology and Bioengineering 78.4 (2002): 442-453. (Year: 2002).*
Futrega et al. "Spheroid coculture of hematopoietic stem/progenitor cells and monolayer expanded mesenchymal stem/stromal cells in polydimethylsiloxane microwells modestly improves in vitro hematopoietic stem/progenitor cell expansion." Tissue Engineering Part C: Methods 23.4 (Apr. 1, 2017): 200-218. (Year: 2017).*
Kennedy, Marion, et al. "Development of the hemangioblast defines the onset of hematopoiesis in human ES cell differentiation cultures." Blood 109.7 (2007): 2679-2687. (Year: 2007).*
Kurosawa "Methods for inducing embryoid body formation: in vitro differentiation system of embryonic stem cells." Journal of bioscience and bioengineering 103.5 (2007): 389-398. (Year: 2007).*
Dos Santos et al. "Bioreactor design for clinical-grade expansion of stem cells." Biotechnology journal 8.6 (2013): 644-654. (Year: 2013).*
Sivalingam et al. "Superior red blood cell generation from human pluripotent stem cells through a novel microcarrier-based embryoid body platform." Tissue Engineering Part C: Methods 22.8 (2016): 765-780. (Year: 2016).*
Lim et al. "Hematopoietic cell differentiation from embryonic and induced pluripotent stem cells." Stem Cell Research & Therapy 4 (2013): 1-11. (ref of record) (Year: 2013).*
Ackermann et al., "Lost in Translation: Pluripotent Stem Cell-Derived Hematopoiesis," *EMBO Molecular Medicine*, 7(11): 1388-1402 (2015).
"AggreWell™," printed from www.stemcell.com/products/brands/aggrewell.html on Jun. 14, 2017, 4 pages.

(Continued)

*Primary Examiner* — Emily A Cordas
(74) *Attorney, Agent, or Firm* — Leydig, Voit & Mayer, Ltd.

(57) ABSTRACT

Disclosed are methods of preparing CD34+CD43+ hematopoietic progenitor cells (HPC) in vitro according to embodiments of the invention. Also disclosed are methods of differentiating CD34+CD43+ hematopoietic progenitor cells to hematopoietic lineage cells according to embodiments of the invention. Also disclosed are methods of treating or preventing a condition in a mammal, e.g., cancer, according to embodiments of the invention.

13 Claims, 28 Drawing Sheets

(56) References Cited

OTHER PUBLICATIONS

Anderson et al., "Fetal thymus organ culture," *CSH Protoc.*, 6 pages (2007).
Awong et al., "Characterization in Vitro and Engraftment Potential In Vivo of Human Progenitor T Cells Generated from Hematopoietic Stem Cells," *Blood*, 114(5): 972-982 (2009).
Barberi et al., "Mesenchymal Cells," *Methods in Enzymology*, 418: 194-208 (2006).
Choi et al., "Hematopoietic and Endothelial Differentiation of Human Induced Pluripotent Stem Cells," *Stem Cells*, 27: 559-567 (2009).
Cobaleda et al., Conversion of Mature B Cells into T Cells by Dedifferentiation to Uncommitted Progenitors, *Nature*, 449: 473-477 (2007).
Crompton et al., "Memoirs of a Reincarnated T Cell," *Stem Cell Cell*, 12: 6-8 (2013).
Crompton et al., "Reprogramming Antitumor Immunity," *Trends Immunol.*, 35(4): 178-185 (2014).
European Patent Office, International Search Report in PCT/US2018/059856 dated Jan. 30, 2019.
European Patent Office, Written Opinion of the International Searching Authority in PCT/US2018/059856 dated Jan. 30, 2019.
Futrega et al., "Spheroid Coculture of Hematopoietic Stem/Progenitor Cells and Monolayer Expanded Mesenchymal Stem/Stromal Cells in Polydimethylsiloxane Microwells Modestly Improves In Vitro Hematopoietic Stem/Progenitor Cell Expansion," *Tissue Engineering*, 23(4): 200-218 (2017).
Galić et al., "T Lineage Differentiation From Human Embryonic Stem Cells," *PNAS* 103(31): 11742-11747 (Aug. 1, 2006).
Hanna et al., "Somatic Cell Reprogramming and Transitions Between Pluripotent States: Facts, Hypotheses, Unresolved Issues," *Cell*, 143(4): 508-525 (2010).
Jopling et al., "Dedifferentiation, Transdifferentiation and Reprogramming: Three Routes to Regeneration," *Nat. Rev. Mol. Cell Biol.*, 12: 79-89 (2011).
Kennedy et al., "T Lymphocyte Potential Marks the Emergence of Definitive Hematopoietic Progenitors in Human Pluripotent Stem Cell Differentiation Cultures," *Cell Reports*, 2: 1722-1735 (Dec. 27, 2012).
Li et al., "Hematopoietic Cells from Primate Embryonic Stem Cells," *Methods in Enzymology*, 418: 243-251 (2006).
Lim et al., "Hematopoietic Cell Differentiation from Embryonic and Induced Pluripotent Stem Cells," *Stem Cell Research & Therapy*, 4(71): 1-11 (2013).
Mehrasa et al., "Mesenchymal Stem Cells as a Feeder Layer Can Prevent Apoptosis of Expanded Hematopoietic Stem Cells Derived from Cord Blood," *Int. J. Mol. Cell Med.*, 3(1): 1-10 (2014).
Nishimura et al., "Generation of Rejuvenated Antigen-Specific T Cells by Reprogramming to Pluripotency and Redifferentiation," *Cell Stem Cell*, 12: 114-126 (2013).
Nishizawa et al., "Epigenetic Variation between Human Induced Pluripotent Stem Cell Lines is an Indicator of Differentiation Capacity," *Cell Stem Cell*, 19: 341-354 (Sep. 1, 2016).
Ogle et al., "Biological Implications of Cell Fusion," *Nat. Rev. Mol. Cell Biol.*, 6: 567-75 (2005).
Salvagiotto et al., "A Defined Feeder-Free, Serum-Free System to Generate In Vitro Hematopoietic Progenitors and Differentiated Blood Cells from hESCs and hiPSCs," *PLoS One*, 6(3): 1-9 (Mar. 2011).
Serwold et al., "Early TCR Expression and Aberrant T Cell Development in Mice with Endogenous Prerearranged T Cell Receptor Genes," *J. Immunol.*, 179: 928-938 (2007).
Stadtfeld et al., Induced Pluripotency: History, Mechanisms, and Applications, *Genes Dev.*, 24: 2239-2263 (2010).
Suzuki et al., "Generation of Engraftable Hematopoietic Stem Cells from Induced Pluripotent Stem Cells by Way of Teratoma Formation," *Molecular Therapy*, 21(7): 1424-1431 (Jul. 2013).
Szabo et al., Direct Conversion of Human Fibroblasts to Multilineage Blood Progenitors, *Nature*, 468: 521-26 (2010).
Takebe et al., "Massive and Reproducible Production of Liver Buds Entirely from Human Pluripotent Stem Cells," *Cell Rep.*, 21(10): 2661-2670 (2017).
Tamaoki et al., "Dental Pulp Cells for Induced Pluripotent Stem Cell Banking," *J. Dent. Res.*, 89(8): 773-778 (2010).
Timmermans et al., "Generation of T Cells from Human Embryonic Stem Cell-Derived Hematopoietic Zones," *The Journal of Immunology*, 182(11): 6879-6888 (2009).
Themeli et al., "New Cell Sources for T Cell Engineering and Adoptive Immunotherapy," *Cell Stem Cell*, 16(4): 357-66 (2015).
Themeli et al., "Generation of Tumor-Targeted Human T Lymphocytes for Induced Pluripotent Stem Cells for Cancer Therapy," *Nature Biotechnol.*, 31(10): 928-933 (2013).
Trivedi et al., "Simultaneous Generation of $CD34^+$ Primitive Hematopoietic Cells and $CD73^+$ Mesenchymal Stem Cells from Human Embryonic Stem Cells Cocultured with Murine OP9 Stromal Cells," *Experimental Hematology*, 35:146-154 (2007).
Uenishi et al., "Tenascin C Promotes Hematoendothelial Development and T Lymphoid Commitment from Human Pluripotent Stem Cells in Chemically Defined Conditions," *Stem Cell Reports*, 3: 1073-84 (2014).
Vizcardo et al., "Generation of Tumor Antigen-Specific iPSC-Derived Thymic Emigrants Using a 3D Thymic Culture System," *Cell Reports*, 22: 3175-3190 (2018).
Vizcardo et al., "Regeneration of Human Tumor Antigen-Specific T Cells from iPSCs Derived from Mature $CD8^+$ Stem Cells," *Cell Stem Cell*, 12: 31-36 (2013).
Wilmut et al., "Viable Offspring Derived from Fetal and Adult Mammalian Cells," *Nature*, 385: 810-813 (1997).
Woods et al., "Brief Report: Efficient Generation of Hematopoietic Precursors and Progenitors from Human Pluripotent Stem Cell Lines," *Stem Cells*, 29: 1158-64 (2011).
Xie et al., "Stepwise Reprogramming of B Cells into Macrophages," *Cell*, 117: 663-676 (2004).
Yuan et al., "Lin28b Reprograms Adult Bone Marrow Hematopoietic Progenitors to Mediate Fetal-Like Lymphopoiesis," *Science*, 335(6073): 1195-1200 (2012).
Zhao et al., "Extrathymic Generation of Tumor-Specific T Cells from Genetically Engineered Human Hematopoietic Stem Cells via Notch Signaling," *Cancer Res.*, 67(6): 2425-9 (2007).
Zhou et al., "Extreme Makeover: Converting One Cell into Another," *Cell Stem Cell*, 3: 382-388 (2008).

* cited by examiner

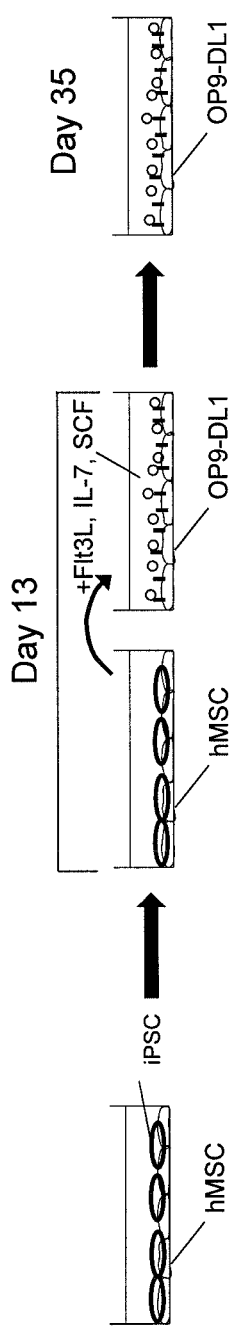
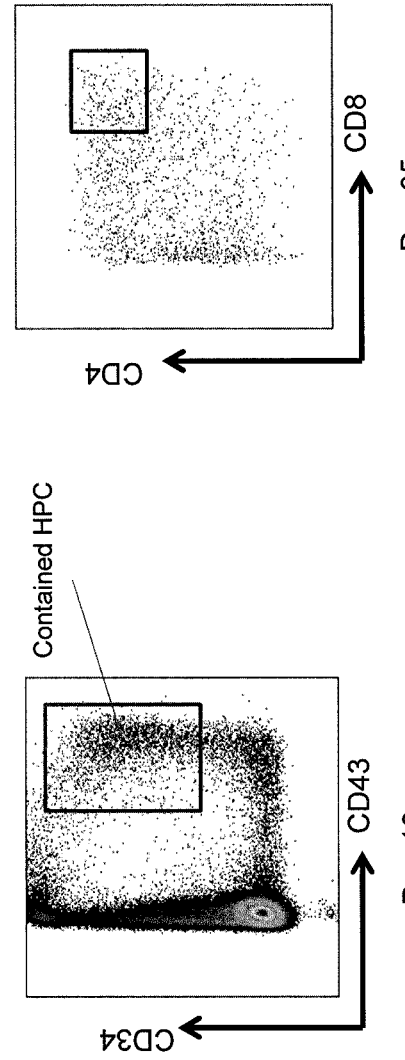
FIG. 1A
FIG. 1B
FIG. 1C

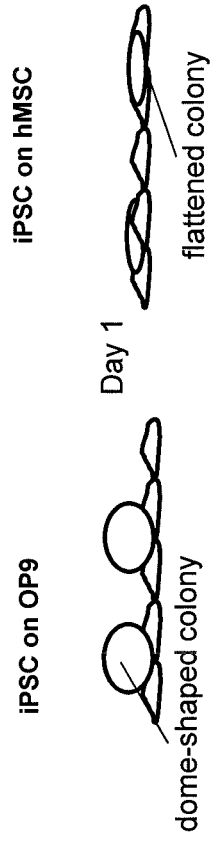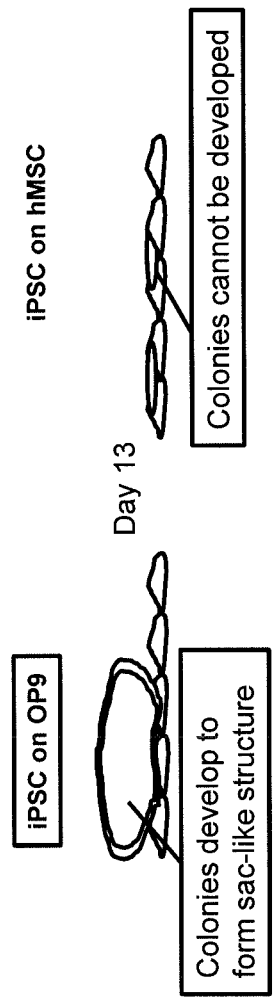
FIG. 2A
FIG. 2B

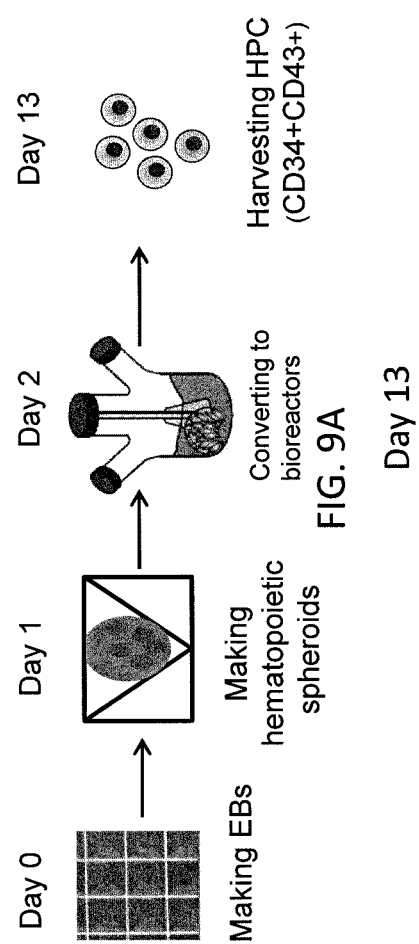
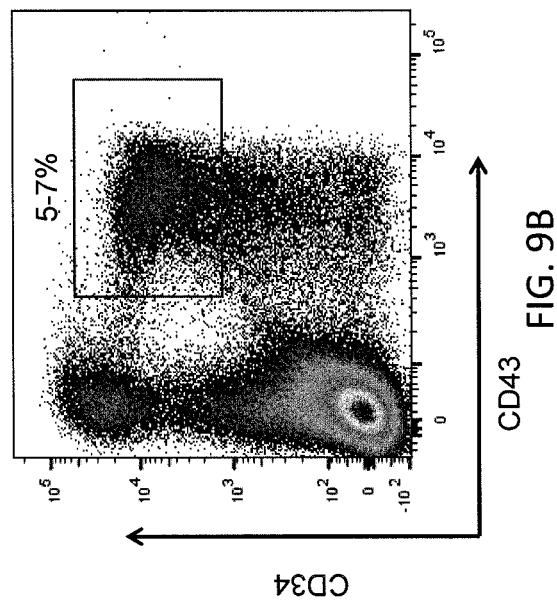
FIG. 9A
FIG. 9B

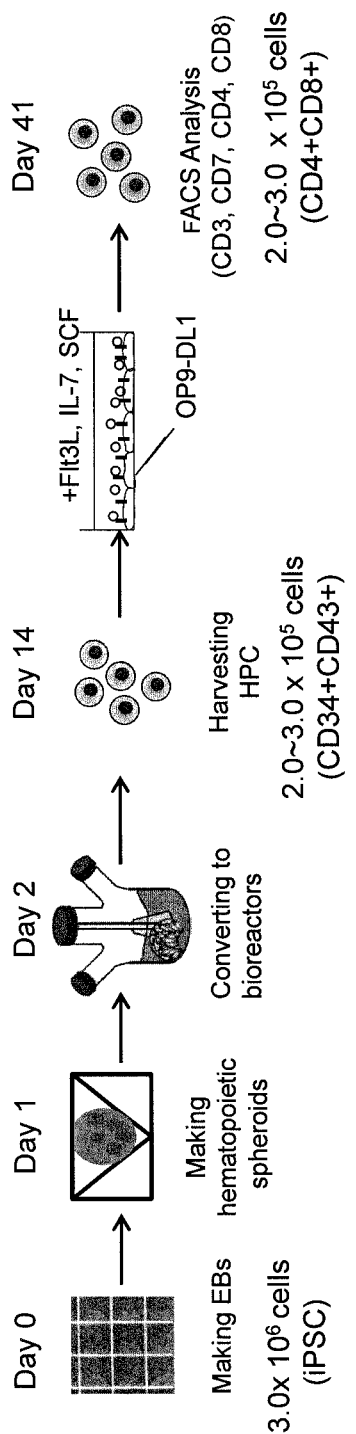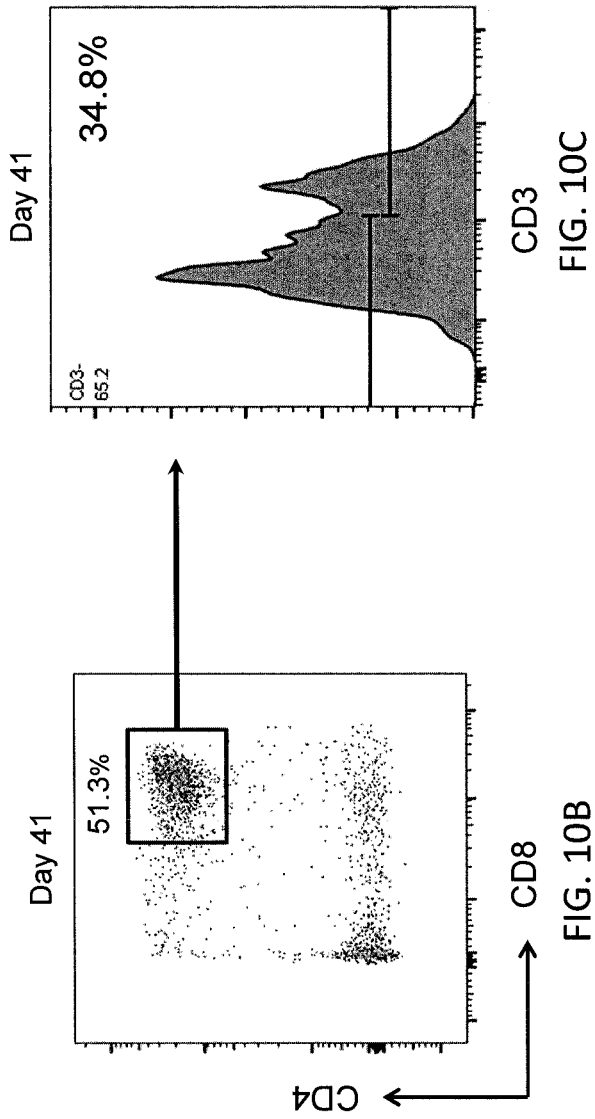
FIG. 10A
FIG. 10B
FIG. 10C

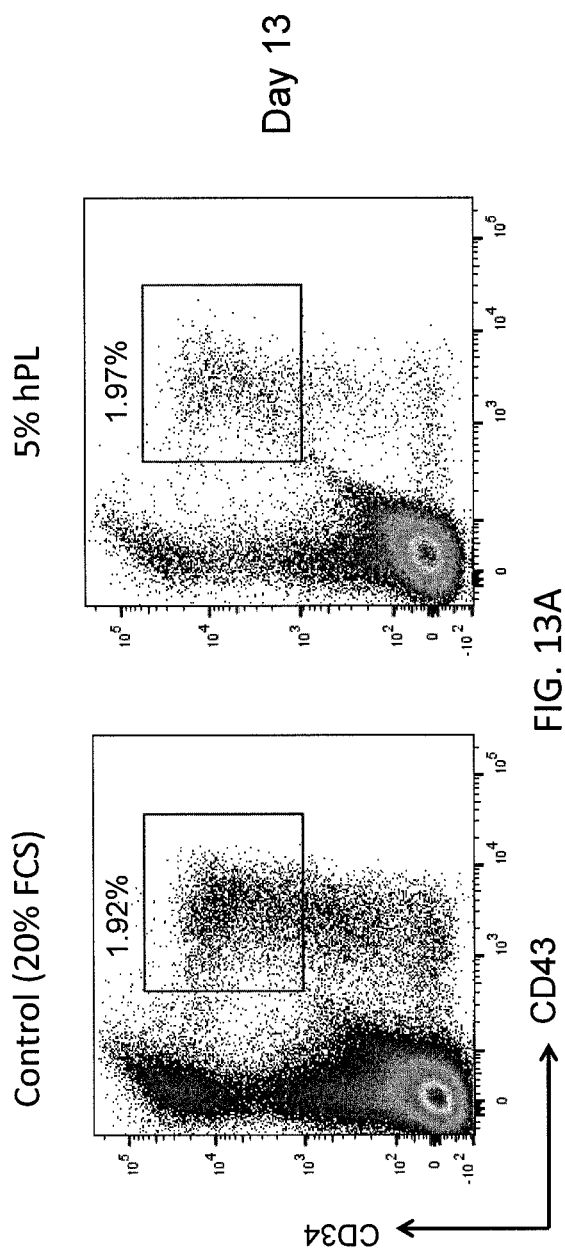
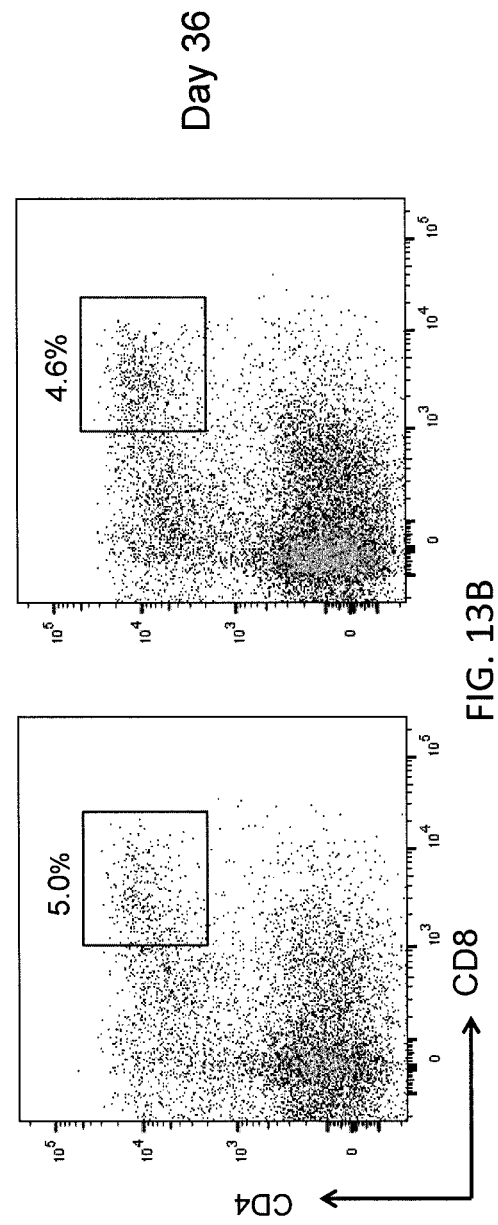
FIG. 13A
FIG. 13B

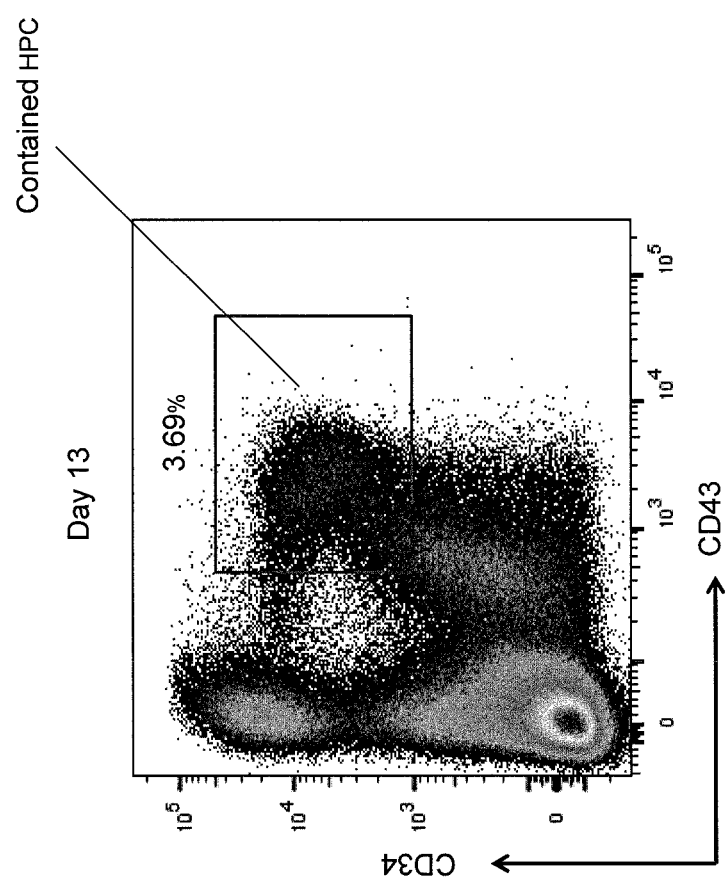

METHODS OF PREPARING HEMATOPOIETIC PROGENITOR CELLS IN VITRO

CROSS-REFERENCE TO RELATED APPLICATION APPLICATIONS

This patent application is a U.S. National Phase Patent Application of International Patent Application No. PCT/US2018/059856, filed Nov. 8, 2018, which claims the benefit of U.S. Provisional Patent Application No. 62/583,240, filed Nov. 8, 2017, both of which are incorporated by reference in their entireties herein.

STATEMENT REGARDING FEDERALLY SPONSORED RESEARCH AND DEVELOPMENT

This invention was made with Government support under project number ZIA BC001076312 by the National Institutes of Health, National Cancer Institute. The Government has certain rights in the invention.

BACKGROUND OF THE INVENTION

Multi-potential hematopoietic progenitor cells (HPC) may be used in adoptive cell therapy (ACT) for the treatment of a variety of disorders, e.g., cancer. However, obstacles to the in vitro production of these cells remain. Accordingly, there is a need for improved materials and methods useful for preparing HPC for use in ACT.

BRIEF SUMMARY OF THE INVENTION

An embodiment of the invention provides a method of preparing CD34+CD43+ hematopoietic progenitor cells (HPC) in vitro, the method comprising: culturing source cells in a vessel; collecting the source cells from the vessel and preparing a single cell suspension of source cells; culturing the single cell suspension in a first three-dimensional (3D) culture and forming embryoid bodies (EBs) from the source cells in the first 3D culture; collecting the EBs, mixing the EBs with mesoderm lineage cells (MLC), and preparing a single cell suspension comprising EBs and MLC; co-culturing the EBs and MLC in the single cell suspension in a second 3D culture and forming hematopoietic spheroids in the second 3D culture; collecting the hematopoietic spheroids from the second 3D culture and culturing the hematopoietic spheroids in a third 3D culture; and harvesting CD34+CD43+ hematopoietic progenitor cells from the hematopoietic spheroids.

Another embodiment of the invention provides a method of preparing CD34+CD43+ HPC in vitro, the method comprising forming source cells into spheroids in a bioreactor by culturing the source cells in suspension in the bioreactor; collecting the spheroids from the bioreactor and mixing the spheroids with MLC; co-culturing the spheroids with the MLC in a first 3D culture and forming hematopoietic spheroids in the first 3D culture; collecting the hematopoietic spheroids from the first 3D culture and culturing the hematopoietic spheroids in a second 3D culture; and harvesting CD34+CD43+ hematopoietic progenitor cells from the hematopoietic spheroids.

Further embodiments of the invention provide methods of treating or preventing a condition in a mammal, the method comprising: preparing HPC in vitro by any of the inventive methods described herein, and administering the HPC to the mammal in an amount effective to treat or prevent the condition in the mammal.

Further embodiments of the invention provide isolated or purified CD34+CD43+ HPC or an isolated or purified population of cells comprising at least one CD34+CD43+ HPC prepared by the inventive methods described herein.

Additional embodiments of the invention provide methods of treating or preventing a condition in a mammal, the method comprising: preparing HPC in vitro according to any of the inventive methods described herein, and administering the HPC to the mammal in an amount effective to treat or prevent the condition in the mammal.

A further embodiment of the invention provides methods of treating or preventing a condition in a mammal, the method comprising: preparing HPC in vitro according to any of the inventive methods described herein, further differentiating the HPC into any one or more of the following hematopoietic lineage cells: erythroids, granulocytes, megakaryocytes, dendritic cells, platelet cells, B cells, T cells, natural killer (NK) cells, and natural killer T (NKT) cells, and administering any one or more of the hematopoietic lineage cells to the mammal in an amount effective to treat or prevent the condition in the mammal.

BRIEF DESCRIPTION OF THE SEVERAL VIEWS OF THE DRAWING(S)

FIG. 1A is a schematic showing a method of culturing induced pluripotent stem cells (iPSC) on human mesenchymal stem cells (hMSC) as feeder cells and adding the iPSC that were cultured on the hMSC to OP9-DL1 mouse stromal cells in a 2-Dimensional (2D) system on day 13. This is a protocol for generating HPC from human iPSC on day 35.

FIG. 1B depicts experimental data illustrating that cells harvested from using hMSC as feeder cells in a 2D monolayer contained CD34+CD43+ expressing HPC on day 13. The gray box shows the HPC population.

FIG. 1C depicts experimental data illustrating that the cells harvested from using hMSC as feeder cells in a 2D monolayer which contained CD34+CD43+ expressing HPC on day 13 (FIG. 1B) resulted in a lower number of CD4+CD8+ double positive (DP) T cells on day 35.

FIG. 2A is a schematic showing that dome-shaped colonies form on Day 1 of culturing human iPSC on OP9 in a 2D system, and that flattened colonies form on Day 1 of culturing human iPSC on human MSC in a 2D system.

FIG. 2B is a schematic showing that sac-like structures form on Day 13 of culturing human iPSC on OP9, and that colonies do not develop on Day 13 of culturing human iPSC on human MSC.

Figure 7A:
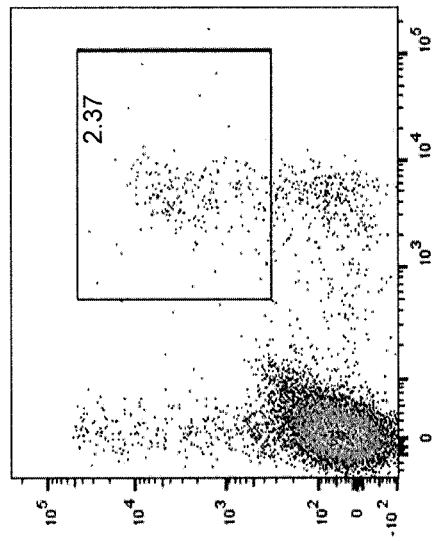
FIG. 7A depicts experimental data illustrating the production of CD34+CD43+ expressing cells from EBs cultured in a 3D hanging drop in the absence of cytokines.
Figure 7B:
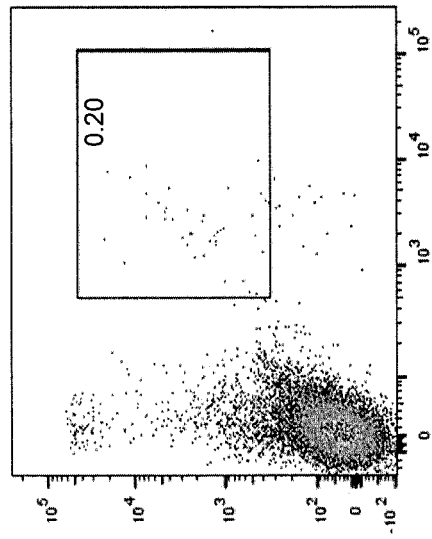
FIG. 7B depicts experimental data illustrating the production of CD34+CD43+ expressing cells from EBs cultured in a 3D hanging drop in the presence of cytokines.
Figure 7C:
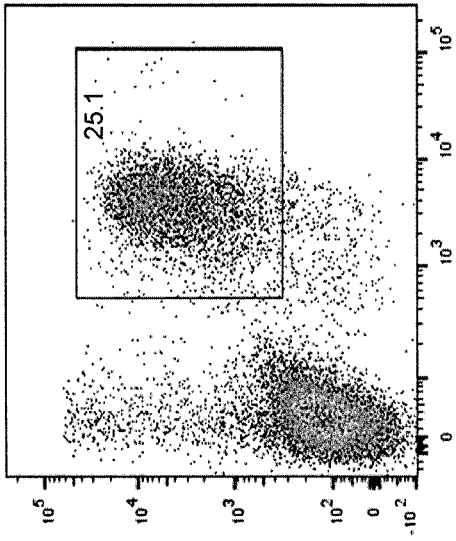
FIG. 7C depicts experimental data illustrating the production of CD34+CD43+ expressing cells from hematopoietic spheroids cultured in a 3D hanging drop in the absence of cytokines.
Figure 7D:
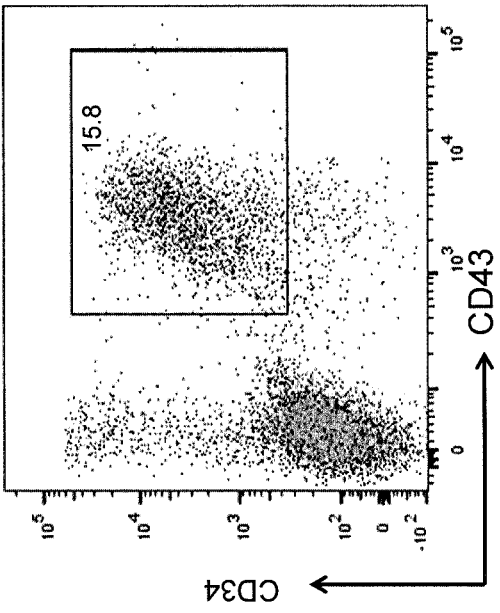
FIG. 7D depicts experimental data illustrating the production of CD34+CD43+ expressing cells from hematopoietic spheroids cultured in a 3D hanging drop in the presence of cytokines.
Figure 7E:
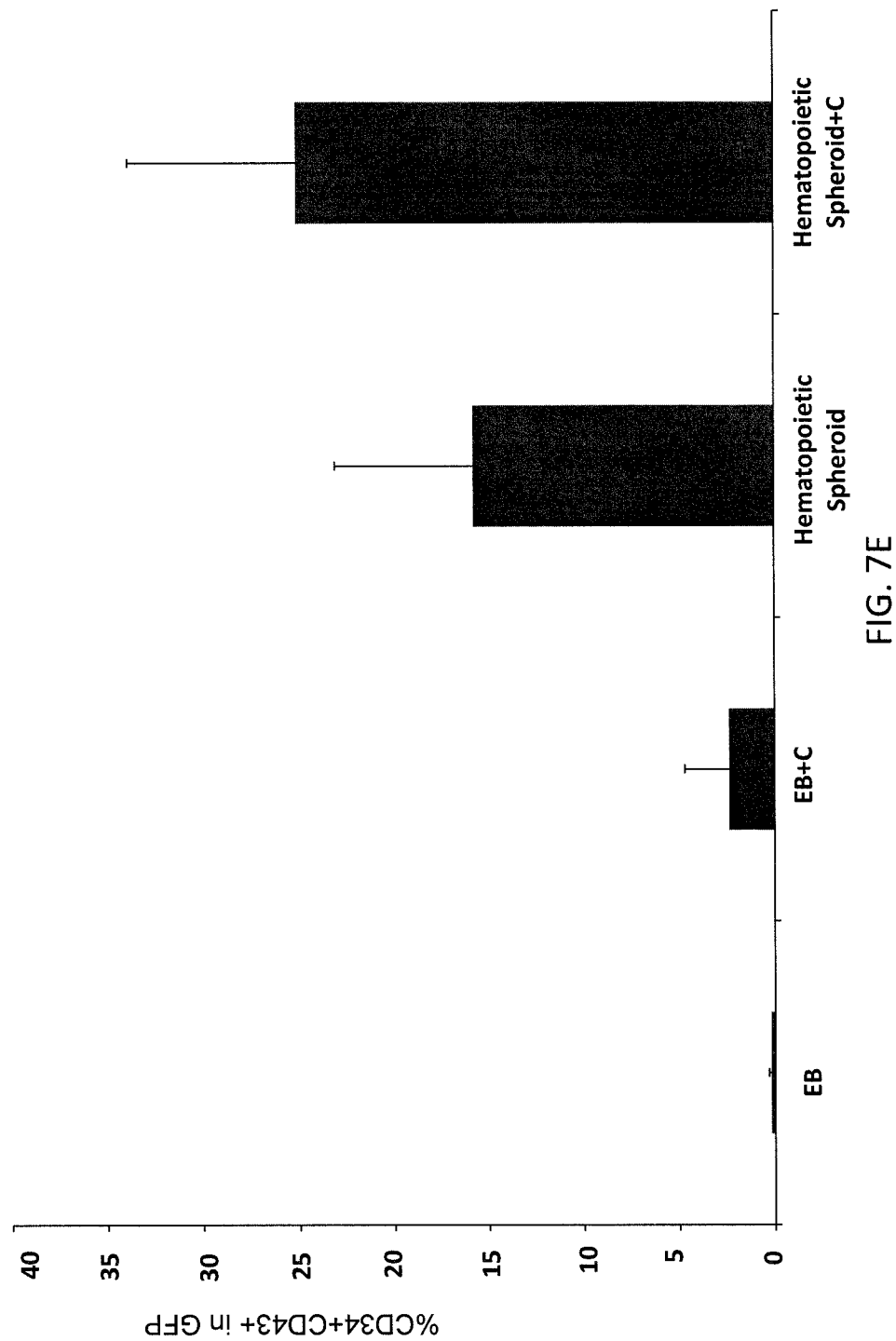

FIG. 7E is a graph depicting the experimental data provided in FIGS. 7A-7D. The y-axis provides the % of CD34+CD43+ cells in green fluorescent protein (GFP) positive cells. The x-axis provides the groups of cells tested (EBs, EBs+ cytokines, hematopoietic spheroids, and hematopoietic spheroids+ cytokines, respectively).

Figure 8A:
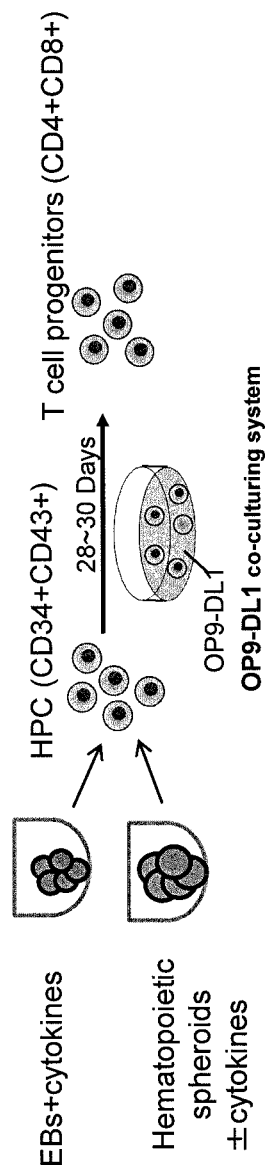

FIG. 8A is a schematic showing a method of producing CD34+CD43+ HPC by culturing human iPSC-derived EBs in the presence of cytokines, and hematopoietic spheroids in the presence of or in the absence of cytokines, according to an embodiment of the invention. As shown, the CD34+CD43+ HPC are added to a mouse OP9-DL1 2D co-culturing system for about 28-30 days for differentiation into DP T cells.

Figure 8B:
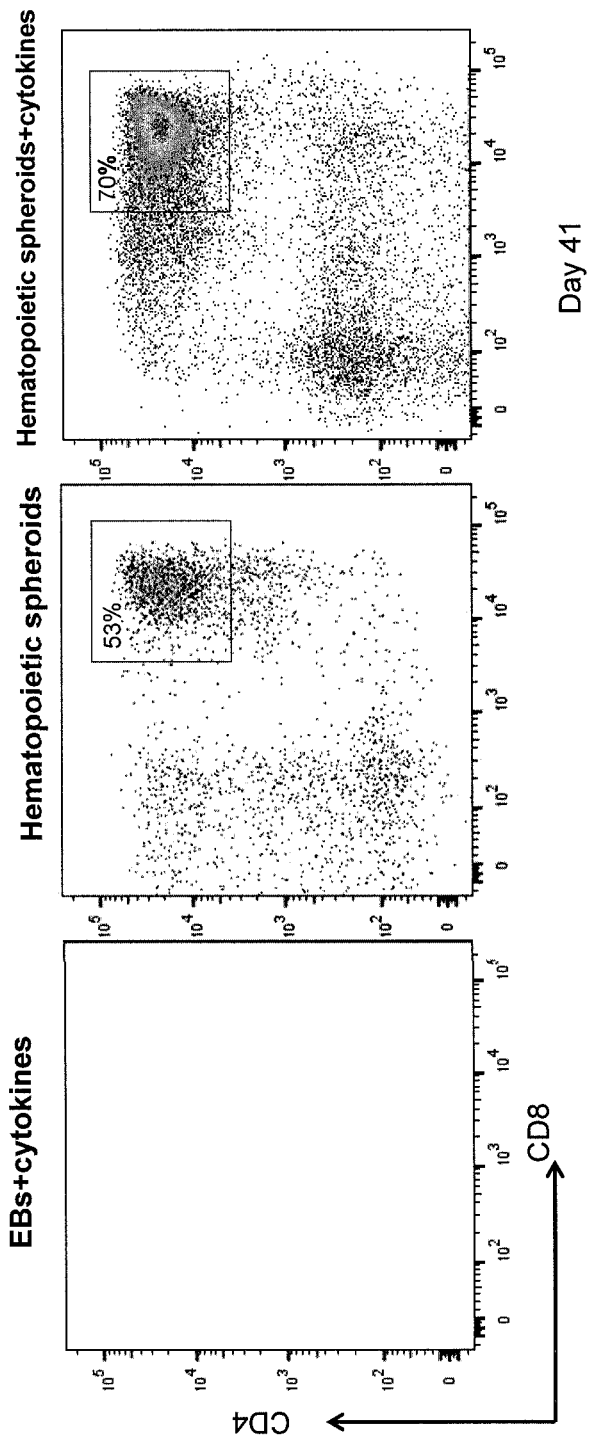

FIG. 8B depicts experimental data illustrating that culturing EBs in the presence of cytokines did not produce any CD4+CD8+ expressing cells (0 cells) at day 41, 53% of cells derived from hematopoietic spheroids cultured in the absence of cytokines expressed CD4+CD8+ on day 41, and 70% of cells derived from hematopoietic spheroids cultured in the presence of cytokines expressed CD4+CD8+ on day 41 of culture.

FIG. 9A is a schematic showing a method of culturing hematopoietic spheroids in bioreactors and harvesting CD34+CD43+ HPC on day 13 according to an embodiment of the invention.

FIG. 9B depicts experimental data illustrating that 5-7% of cells derived from hematopoietic spheroids cultured in bioreactors express CD34+CD43+ on day 13.

FIG. 10A is a schematic showing hematopoietic spheroids cultured in bioreactors that produce 2.0~3.0×10$^5$ CD34+CD43+ HPC at day 13 are harvested according to an embodiment of the invention. The HPC are added to a mouse OP9-DL1 co-culturing system for differentiation. As shown, fluorescence-activated cell sorting (FACS) analysis revealed cells expressing the T cell markers CD3+, CD7+, CD4+, and CD8+ at day 41. Cells derived from hematopoietic spheroids cultured in bioreactors produce 2.0~3.0×10$^5$ CD4+CD8+ cells according to embodiments of the invention.

FIG. 10B depicts experimental data illustrating the percentage of cells derived from hematopoietic spheroids that express CD4+ and CD8+ on day 41 (51.3%) (shown in the gray box).

FIG. 10C depicts experimental data illustrating the percentage of cells derived from hematopoietic spheroids that express CD3+ on day 41 (34.8%).

Figure 11A:
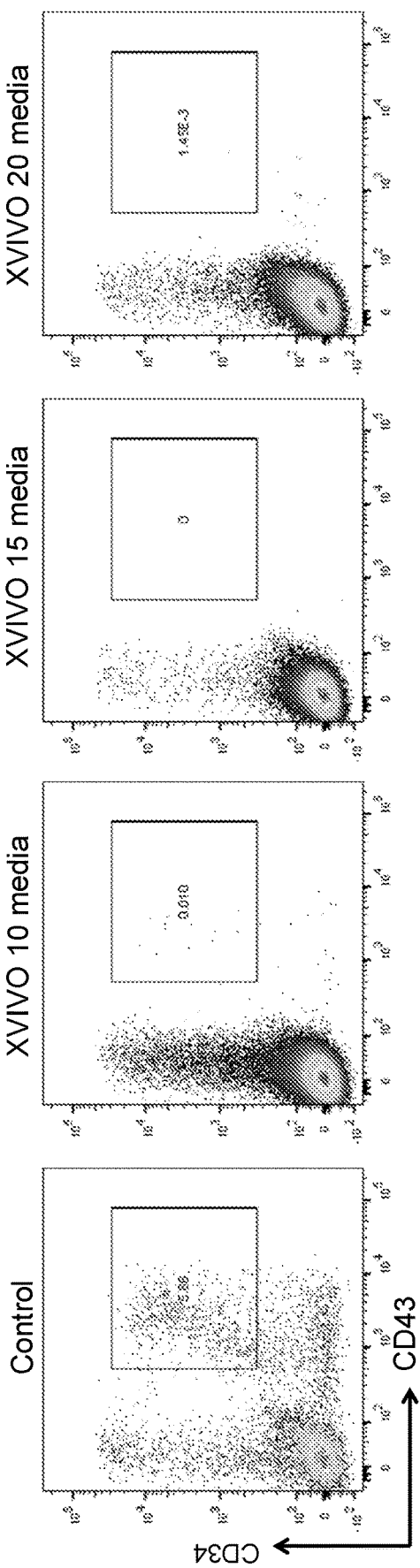

FIG. 11A depicts experimental data illustrating that culturing hematopoietic spheroids in XVIVO 10, XVIVO 15, XVIVO 20 (Lonza, Basel, Switzerland) xeno-free media produced a lower percentage of CD34+CD43+ cells as compared with hematopoietic spheroids cultured in the control media. The numbers in the boxes represent the percentage of cells from hematopoietic spheroids cultured in the indicated media that express CD34+ and CD43+.

Figure 11B:
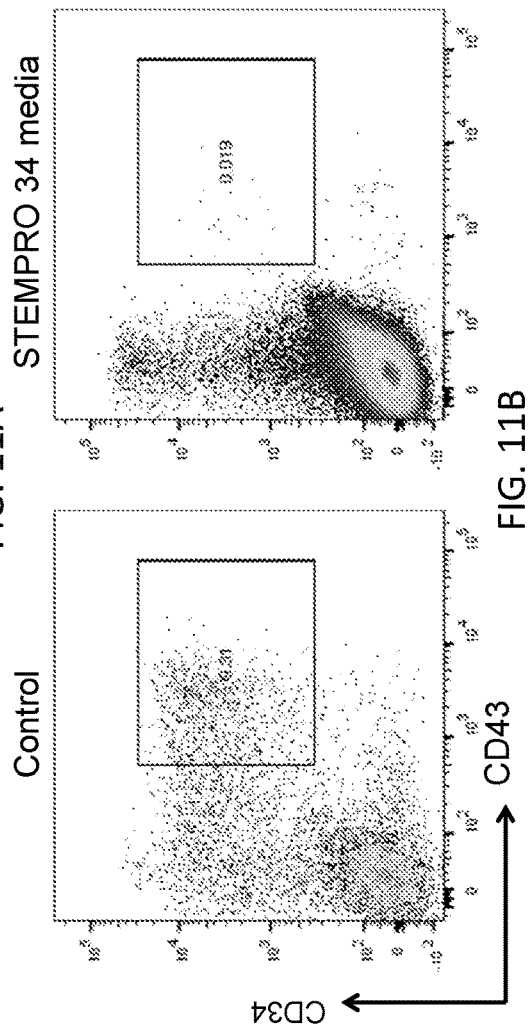

FIG. 11B depicts experimental data illustrating that culturing hematopoietic spheroids in STEMPRO 34 (Thermo Fisher Scientific, Waltham, MA) xeno-free media produced a lower percentage of CD34+CD43+ cells as compared with hematopoietic spheroids cultured in the control media. The numbers in the boxes represent the percentage of cells from hematopoietic spheroids cultured in the indicated media that express CD34+ and CD43+.

Figure 12:
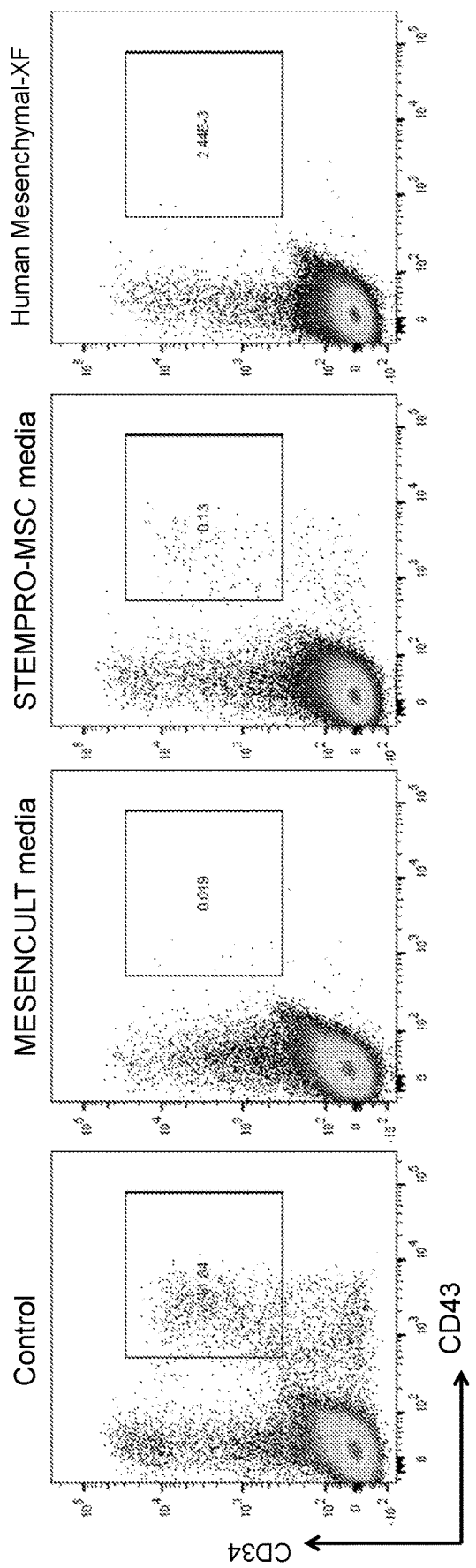

FIG. 12 depicts experimental data illustrating that culturing hematopoietic spheroids in MESENCULT (Stemcell Technologies, Vancouver, BC, Canada), STEMPRO-MSC (Thermo Fisher Scientific), and human MESENCHYMAL-XF (Sigma) xeno-free media produced a lower percentage of CD34+CD43+ as compared with hematopoietic spheroids cultured in the control media. The numbers in the boxes represent the percentage of cells from hematopoietic spheroids cultured in the indicated media that express CD34+ and CD43+.

FIG. 13A depicts experimental data illustrating the percentage of cells expressing CD34+CD43+ resulting from culturing hematopoietic spheroids in the 20% FCS control (1.92% of cells) as compared to culturing in 5% hPL media (1.97% of cells) on day 13.

FIG. 13B depicts experimental data illustrating the percentage of cells expressing CD4+CD8+ resulting from culturing hematopoietic spheroids in the 20% FCS control (5.0% of cells) as compared to culturing in 5% hPL media (4.6% of cells) on day 36.

FIG. 14 depicts experimental data illustrating the percentage of HPCs (3.69%) expressing CD34+CD43+ from human iPSC-derived hematopoietic spheroids on day 13.

Figure 15A:
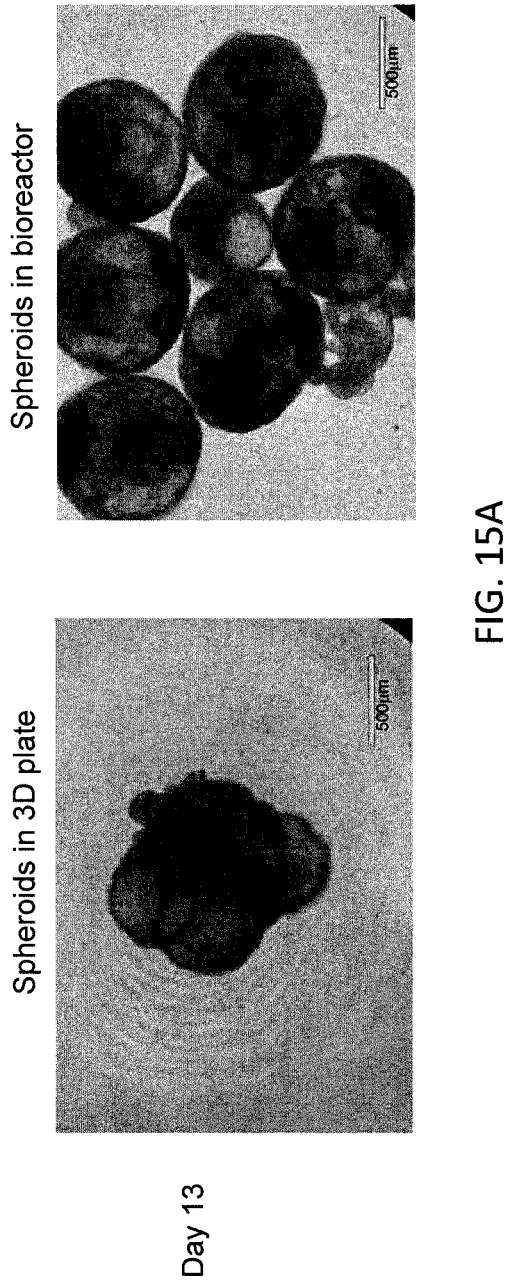
Figure 15B:
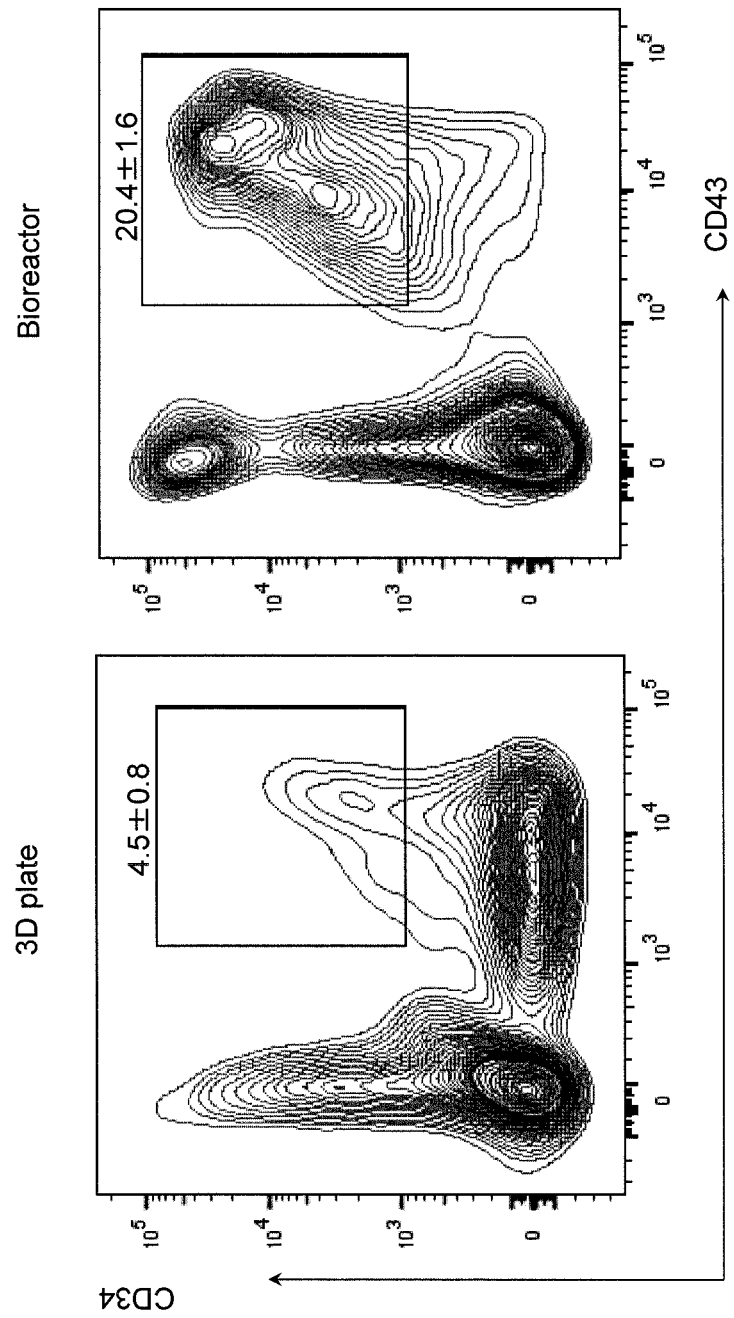
Figures 15C, 15D:
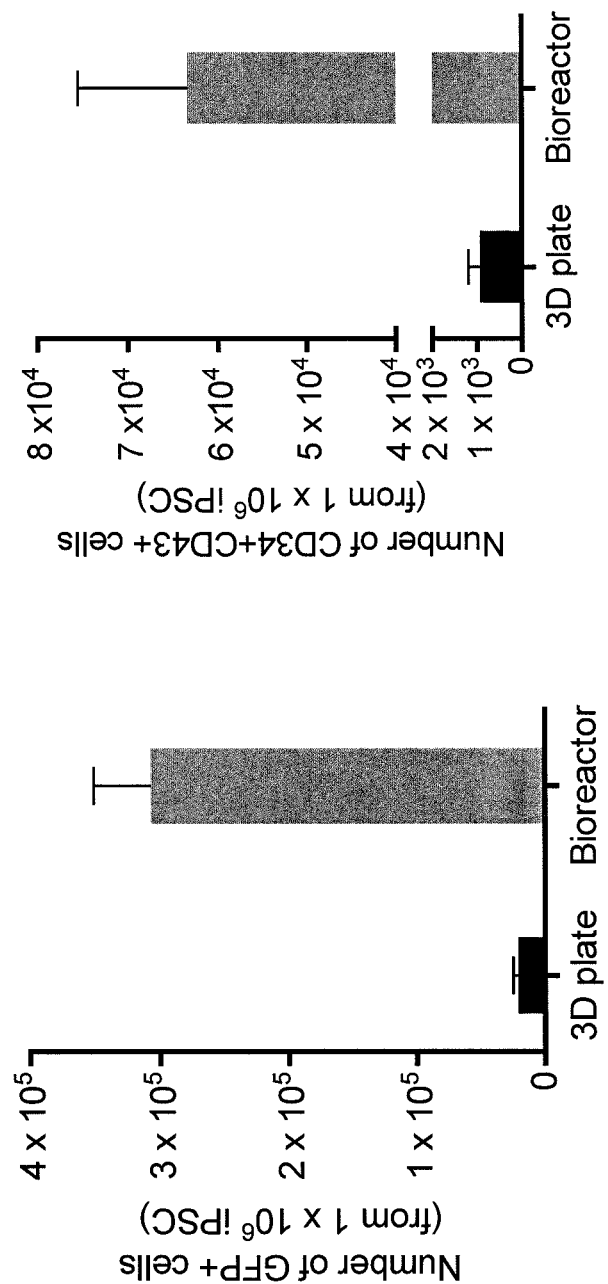

FIGS. 15A-15D depict experimental data and images illustrating that culturing hematopoietic spheroids in stirred-suspension bioreactors can enhance the expansion and differentiation of iPSC as compared to when the hematopoietic spheroids are cultured in a 3D plate. FIG. 15A illustrates that the hematopoietic spheroids in the stirred-suspension bioreactors are more differentiated than the hematopoietic spheroids in a 3D plate at day 13 of culture. FIG. 15B illustrates these results by flow cytometry. FIGS. 15C and 15D illustrate these results in graph form.

Figure 16A:
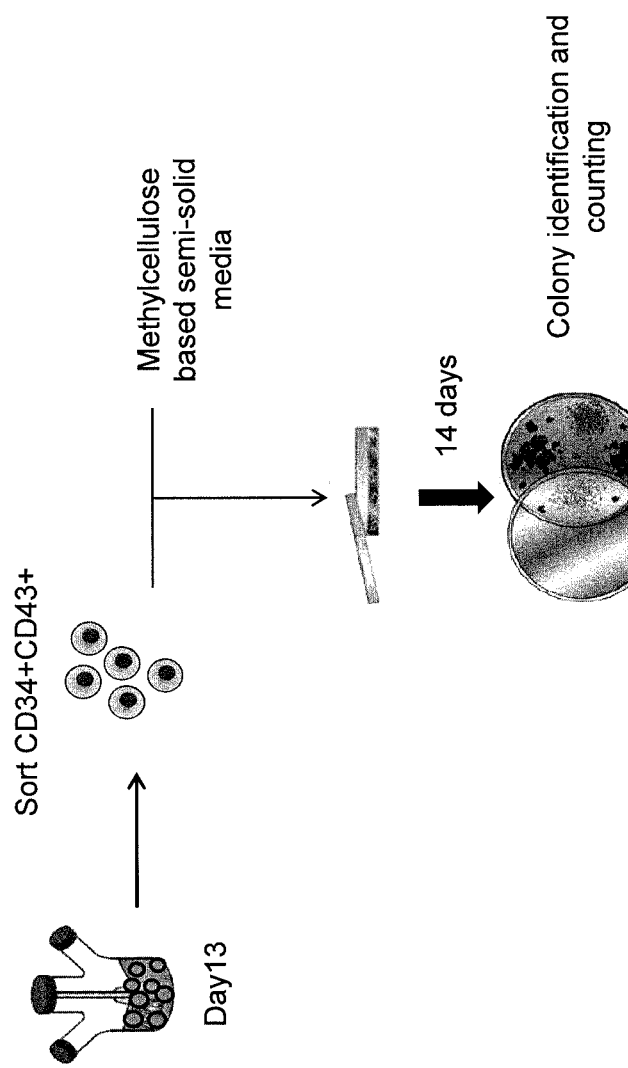
Figure 16B:
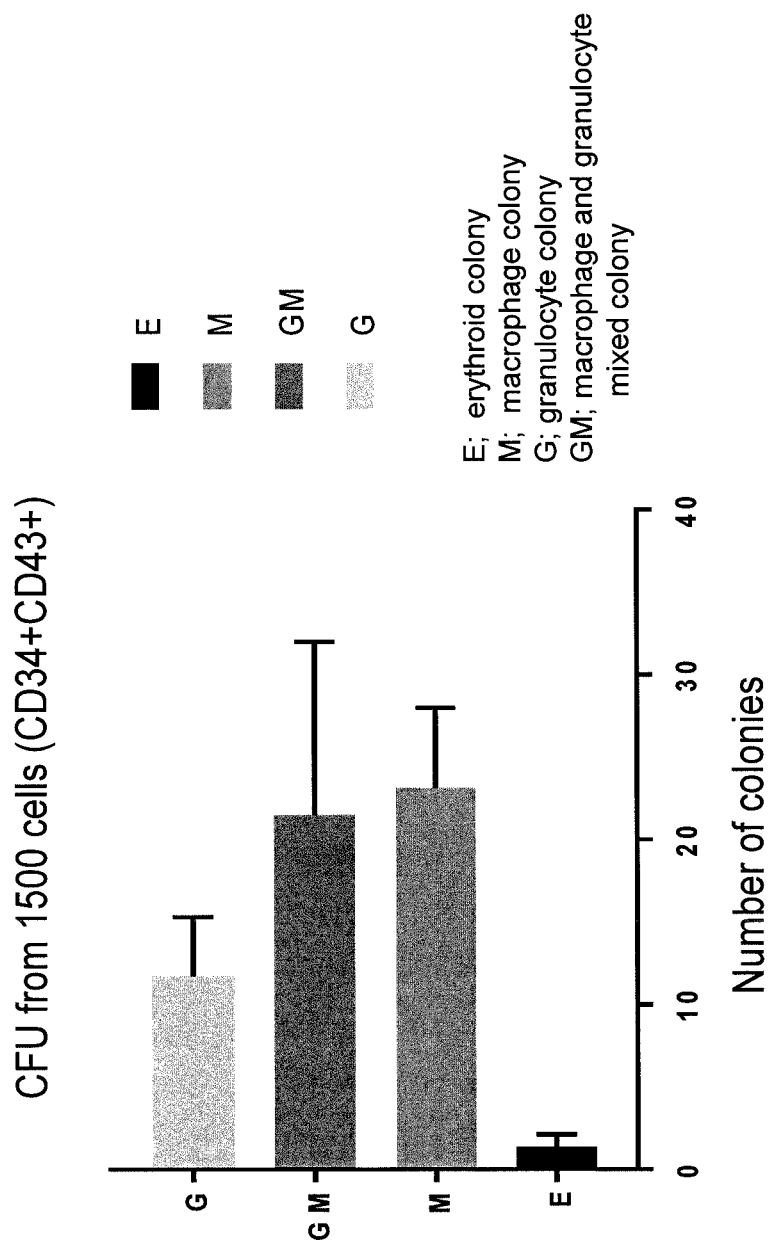

FIGS. 16A-16B depict a flowchart and experimental data illustrating that the hematopoietic spheroids can differentiate into myeloid lineage cells. CD34+CD43+ cells from hematopoietic spheroids were cultured and after 14 days colonies of erythriods, macrophages, and granulocytes were established. FIG. 16A is a schematic illustrating the procedure according to an embodiment of the invention and FIG. 16B illustrates the number of colonies as shown in graph form.

Figure 17:
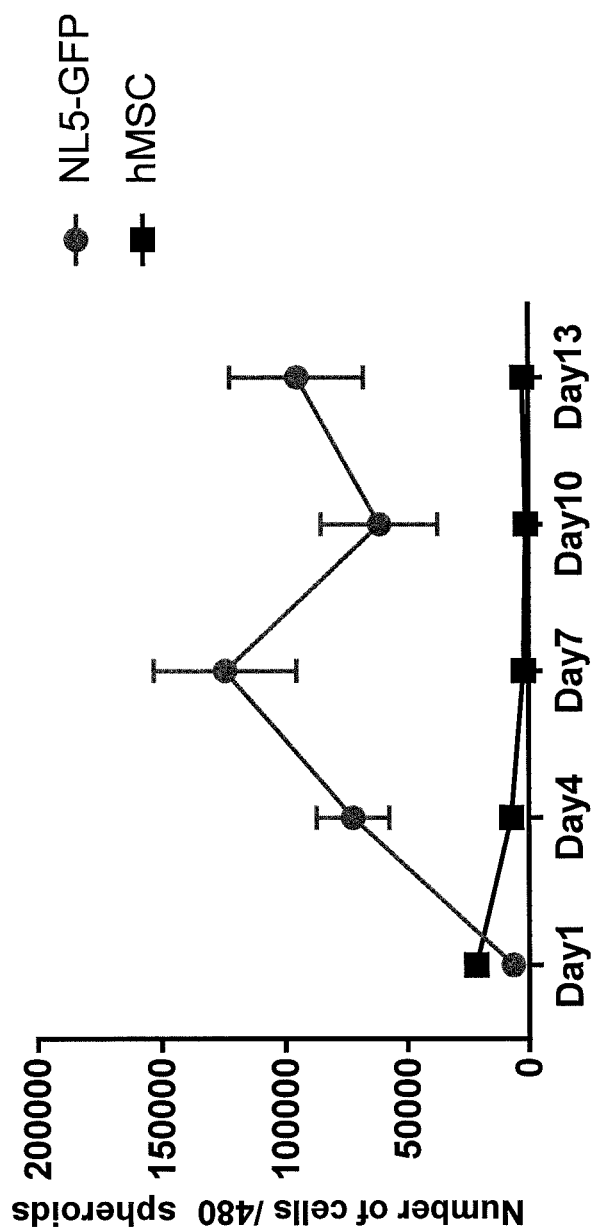

FIG. 17 depicts experimental data illustrating that hematopoietic spheroids largely contain iPSC after 4 days. Specifically, FIG. 17 depicts a graph showing the number of cells per 480 spheroids. The grey line with closed circles represents NL5-GFP and the black line with closed squares represents hMSC.

Figure 18:
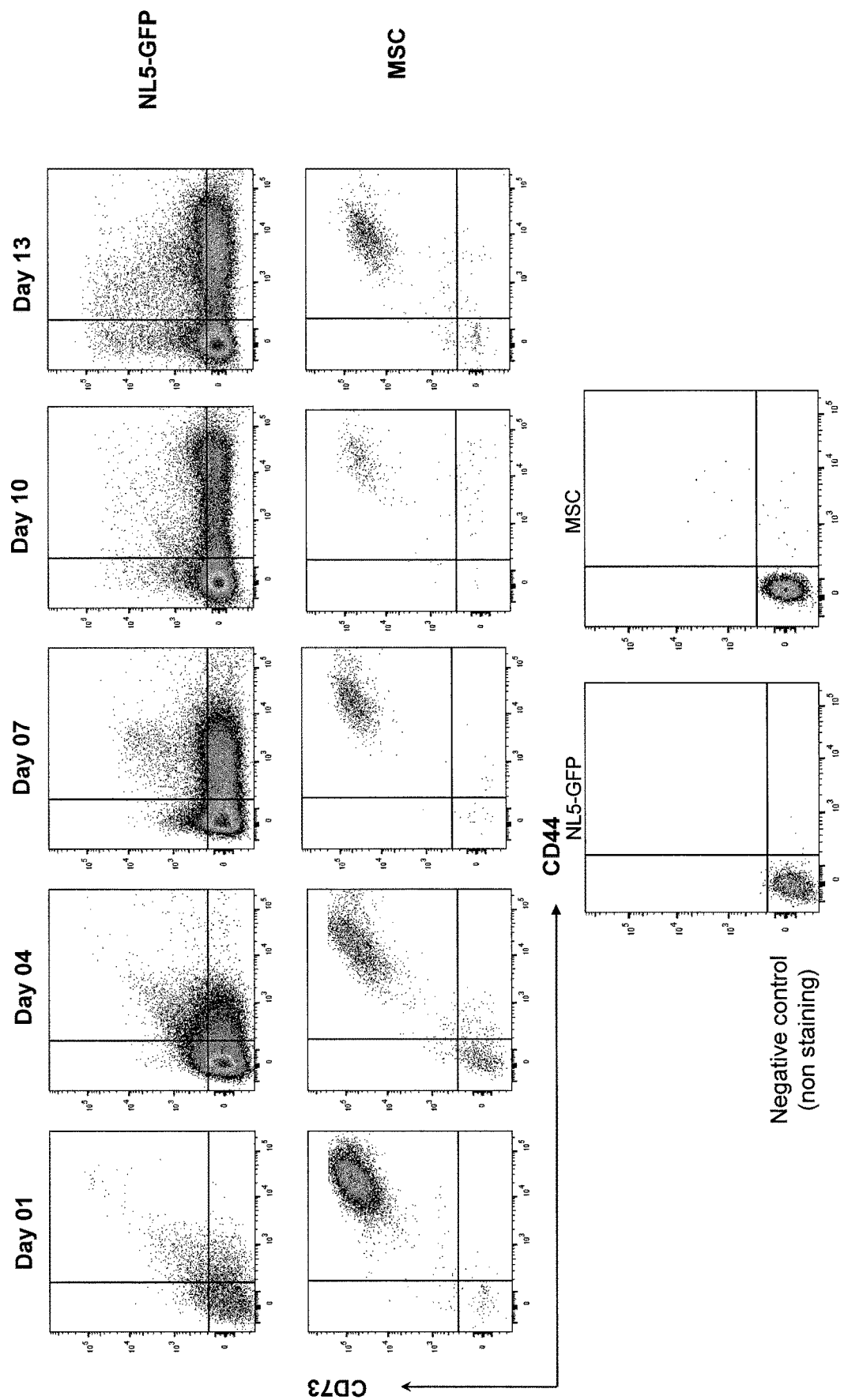

FIG. 18 depicts experimental data illustrating that iPSC-derived CD44+ or CD73+ cells can be detected on day 1 of culture. This indicates that iPSC can generate mesenchymal lineage cells after contacting with hMSC (CD44 and CD73 are markers expressed in stromal cells including hMSC).

NL5-GFP is shown on the top row, the middle row shows MSC, and the control is shown on the bottom row.

Figure 19:
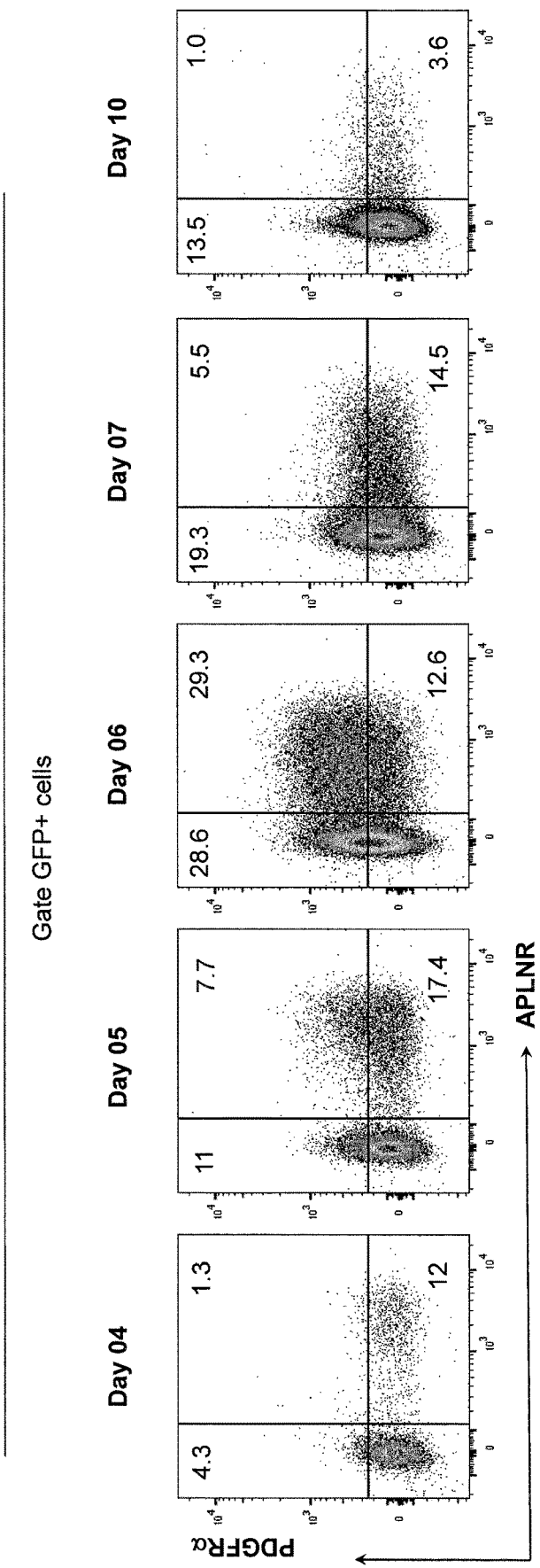

FIG. 19 depicts experimental data illustrating that iPSC in spheroids can progress to the primitive mesoderm stage of development. The top of FIG. 19 shows the flowchart of cell development. The bottom of FIG. 19 shows the percentage of PDGFRα+APLNR+ cells at days 4, 5, 6, 7 and 10.

Figure 20:
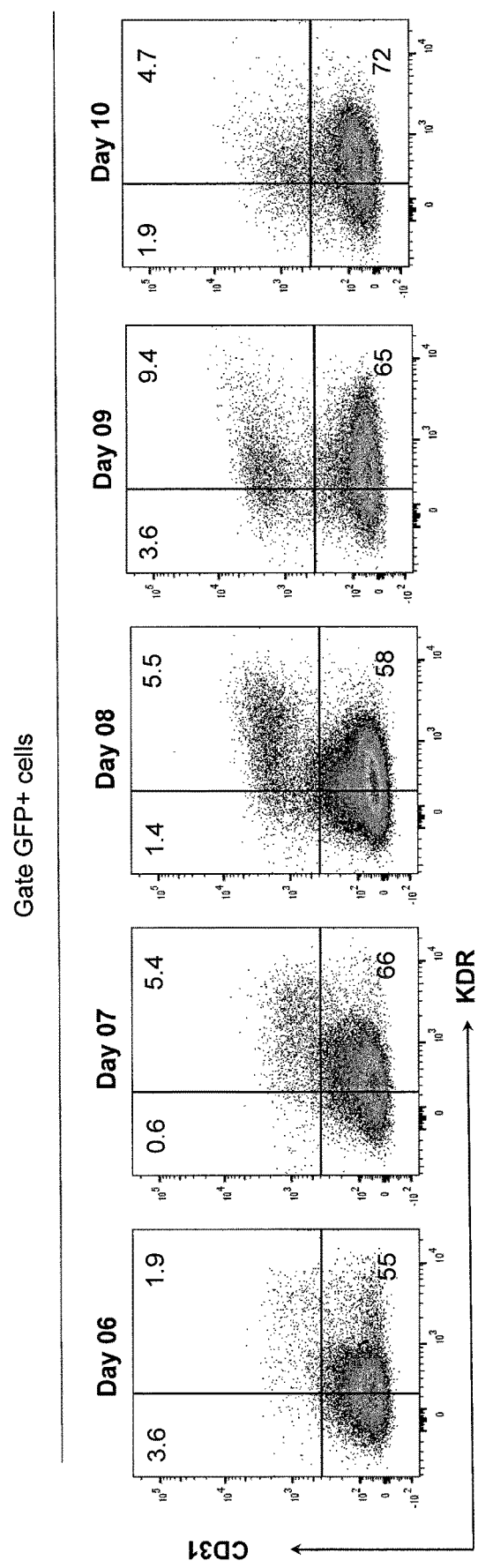

FIG. 20 depicts experimental data illustrating that iPSC in spheroids can further progress to the hemogenic endothelium stage of development. The top of FIG. 20 shows the flowchart of cell development. The bottom of FIG. 20 shows the percentage of CD31+KDR+ cells at days 6, 7, 8, 9 and 10.

Figure 21:
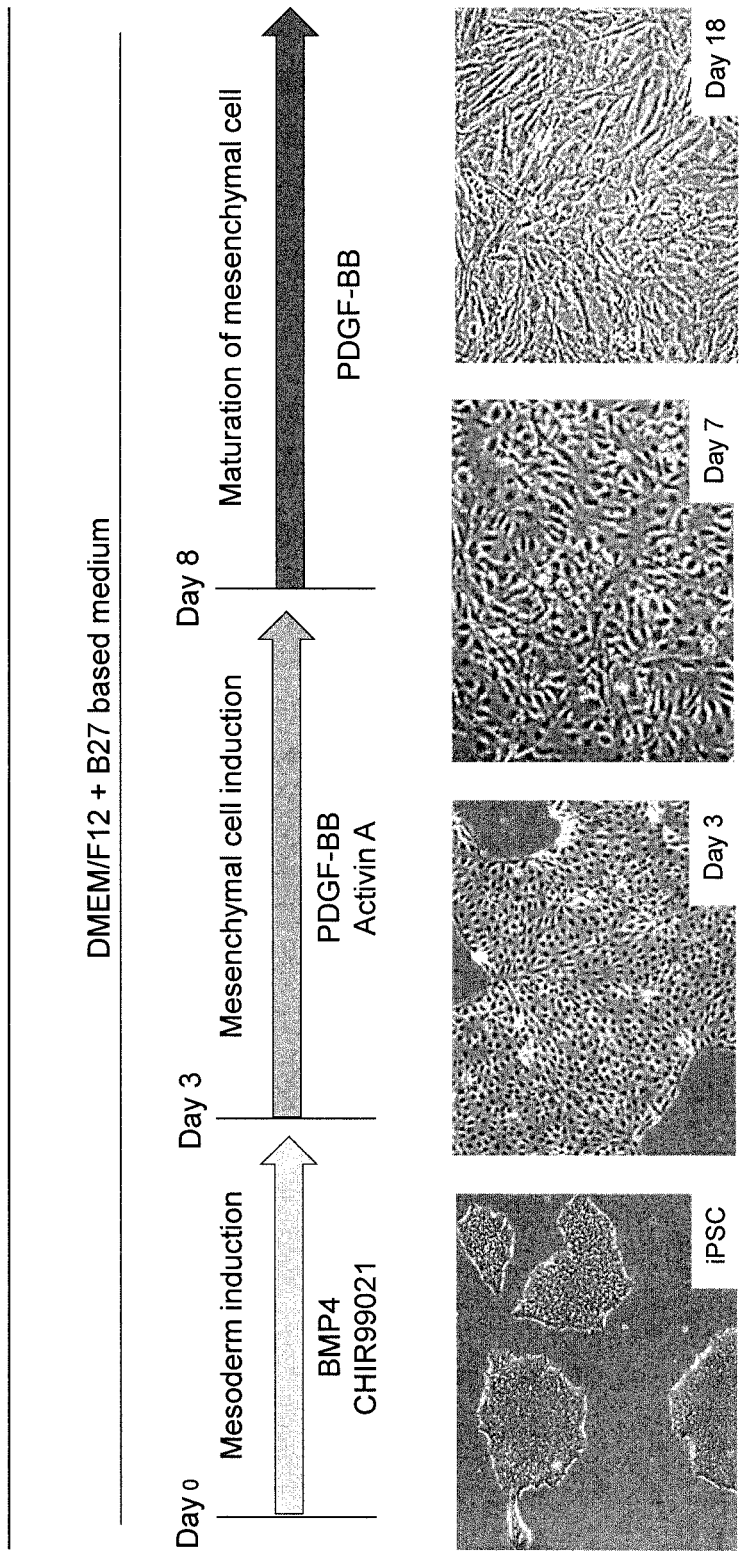

FIG. 21 depicts experimental data illustrating that iPSC derived mesenchymal cells (iMC) can be used for co-culturing with iPSC. The top of FIG. 21 shows the flowchart of cell development: mesoderm induction to mesenchymal cell induction to maturation of mesenchymal cell. The bottom of FIG. 21 illustrates images of the cells at days 3, 7, and 18 of culturing.

Figure 22:
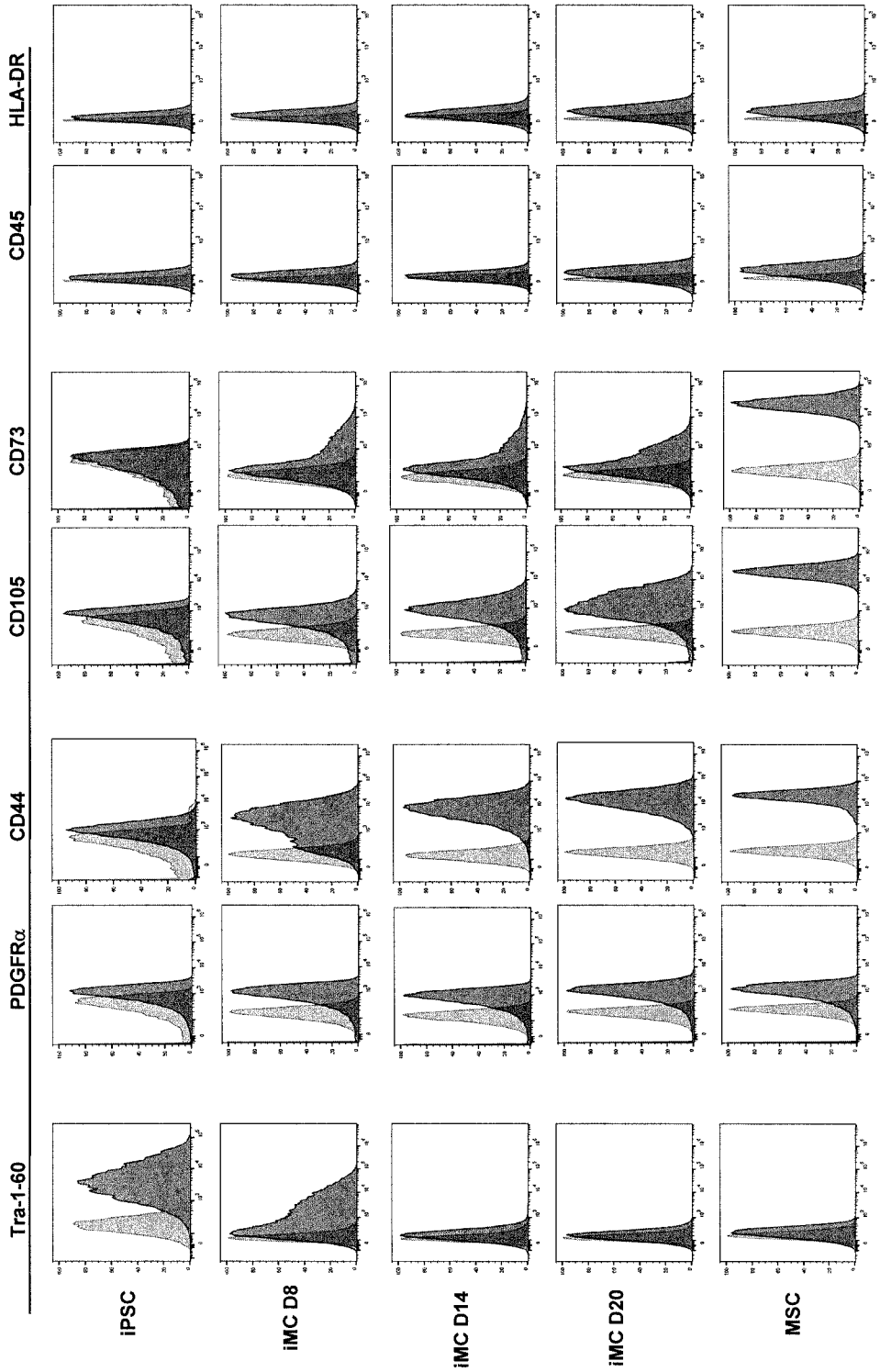

FIG. 22 depicts experimental data illustrating that iPSC derived mesenchymal cells (iMC) share typical MSC markers (left to right: Tra-1-60, PDGFRalpha, CD44, CD105, CD73, CD45, HLA-DR).

Figure 23A:
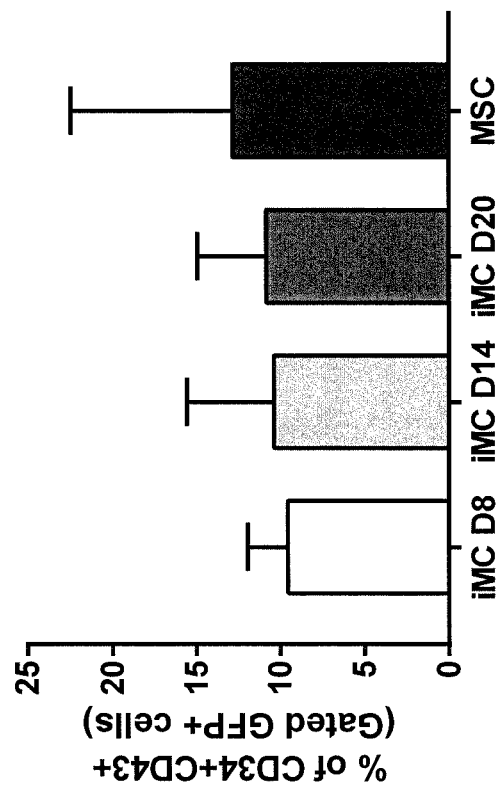
Figure 23B:
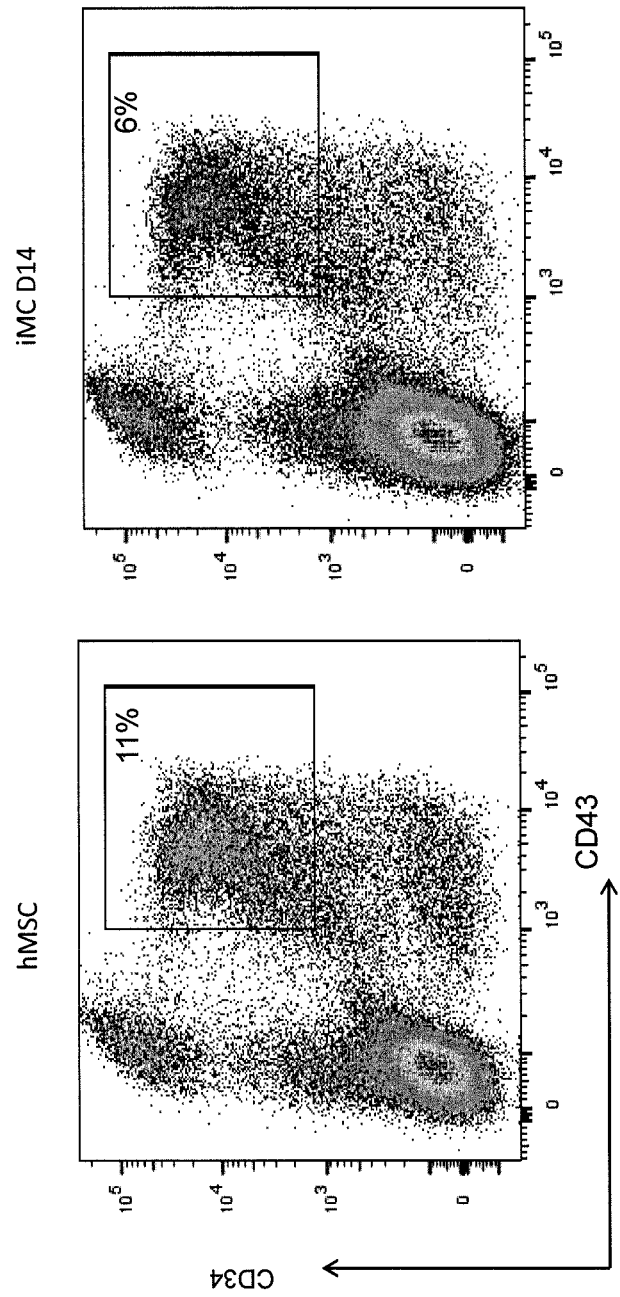

FIGS. 23A-23B depict experimental data illustrating iMC also can iPSC differentiation toward HPC. FIG. 23A is a graph illustrating the number of gated GFP+ cells as a percentage of CD34+CD43+ cells for iMC at days 8, 14, and 20 (left to right: "D8," "D14", and "D20") and MSC. FIG. 23B shows the same data obtained by FACS.

DETAILED DESCRIPTION OF THE INVENTION

An embodiment of the invention provides a method of preparing CD34+CD43+ HPC in vitro. CD34 and CD43 are transmembrane cell surface proteins which represent a marker for primitive HPC in human cord blood. CD34+ and CD43+ HPC can differentiate into any one or more of the following hematopoietic lineage cells: erythroids, granulocytes, megakaryocytes, dendritic cells, platelet cells, B cells, T cells, natural killer (NK) cells, and natural killer T (NKT) cells. Embodiments of the invention may provide any one or more of a variety of advantages. For example, HPC prepared by the inventive methods may be further differentiated into hematopoietic lineage cells which may be useful for treating or preventing a variety of conditions in a mammal, e.g., cancer. Alternatively or additionally, HPC prepared by the inventive methods may advantageously be used for: the generation of blood products of rare blood types for blood banking for the treatment of anemias and other cytopenias; in vitro generation of any class of hematopoietic lineage cells; the generation of an immune system for patients with immunodeficiencies; the generation of hematopoietic lineage cell sub-products such as human serum, antibodies and/or cytokines; the generation of T cells with a TCR specific for cancer or other diseases; treatment for patients with rare blood conditions; treatment for patients with rare infections, and immune system reconstitution after immunodeployment due to, e.g., irradiation or chemotherapy. Alternatively or additionally, the inventive methods may provide the following exemplary advantages: the inventive methods may provide a fully autologous system, which may reduce or eliminate invasive procedures on patients; frozen hMSC may be used which may save time and manpower needed for the continuous culturing of hMSC; and the inventive methods may facilitate the mass production of hMSC for clinical applications.

The method may comprise culturing source cells in a vessel. In embodiments, the source cells are induced pluripotent stem cells (iPSC). In embodiments, the source cells may also comprise human embryonic stem cells (hESC), nuclear transfer-derived human embryonic stem (hESC), extended pluripotent stem cells (EPS), lineage-reprogrammed cells, transdifferentiated cells, dedifferentiated cells, or transdetermined cells. Preferably, the source cells are human cells.

The method may further comprise modifying and/or reprogramming source cells. For example, modifying the source cells may comprise modifying the source cells, e.g., iPSC, into pluripotent cells, multipotent cells, or T-lineage cells. Modifying the source cells may be carried out in a variety of different ways. For example, modifying the source cells may comprise reprogramming the lineage of the source cells into T-lineage cells. In this regard, source cells which are not T cells or T-lineage cells may be reprogrammed to T cells or T-lineage cells. For example, the method may comprise modifying source cells which are mature cancer antigen-specific T cells into less developed (immature) T cells. In additional embodiments, the source cells are iPSC, and the inventive method may further comprise reprogramming human T-cells to produce the iPSC.

Lineage reprogramming refers to the conversion of a cell from one type to another in the same lineage or a different lineage without reversion to pluripotency and is described, for example, in Jopling et al., *Nat. Rev. Mol. Cell Biol.*, 12: 79-89 (2011) and Crompton et al., *Trends Immunol.*, 35(4): 178-185 (2014). Lineage reprogramming may include, for example, transdifferentiation, dedifferentiation or transdetermination.

Transdifferentiation refers to the conversion of one mature cell type to another without a dedifferentiated or pluripotent intermediate and is described, for example, in Jopling et al., *Nat. Rev. Mol. Cell Biol.*, 12: 79-89 (2011) and Crompton et al., *Trends Immunol.*, 35(4): 178-185 (2014). An example of a method for carrying out transdifferentiation is described, for example, in Xie et al., *Cell*, 117: 663-676 (2004).

In dedifferentiation, a terminally differentiated cell reverts to a less-differentiated precursor within its own lineage. Dedifferentiation is described, for example, in Jopling et al., *Nat. Rev. Mol. Cell Biol.*, 12: 79-89 (2011) and Crompton et al., *Trends Immunol.*, 35(4): 178-185 (2014). Examples of methods for carrying out dedifferentiation are described, for example, in Yuan et al., *Science*, 335: 1195-1200 (2012) and Cobaleda et al., *Nature*, 449: 473-477 (2007).

In transdetermination, a cell dedifferentiates to an earlier progenitor (without a pluripotent intermediate) and then switches lineages to differentiate to a cell of a distinct lineage. Transdetermination is described, for example, in Crompton et al., *Trends Immunol.*, 35(4): 178-185 (2014). An example of a method for carrying out transdetermination is described, for example, in Szabo et al., *Nature*, 468: 521-26 (2010).

In an embodiment of the invention, modifying the source cells may comprise modifying the source cells to pluripotent cells or multipotent cells. Pluripotent cells have the capacity to give rise to any of the three germ layers: endoderm, mesoderm, and ectoderm. Pluripotent cells may comprise, for example, stem cells, e.g., embryonic stem cells, nuclear transfer derived embryonic stem cells, induced pluripotent stem cells, etc. Multipotent cells may comprise, for example, hematopoietic stem cells. Modifying, e.g., reprogramming, cells to a pluripotent state refers to the reversion of a cell to a pluripotent cell and is described for example, in Crompton et al., *Trends Immunol.*, 35(4): 178-185 (2014). Exemplary techniques may include somatic cell nuclear transfer (SCNT), cell-cell fusion, and direct reprogramming. Examples of methods for carrying out cell-cell fusion are described, for example, in Ogle et al., *Nat. Rev. Mol. Cell Biol.*, 6: 567-75 (2005) and Zhou et al., *Cell Stem Cell*, 3: 382-388 (2008). Examples of methods for carrying out SCNT are described, for example, in Hanna et al., *Cell*, 143: 508-525 (2010); Stadtfeld et al., *Genes Dev.*, 24: 2239-2263 (2010); Wilmut et al., *Nature*, 385: 810-813 (1997); Vizcardo et al., *Cell Stem Cell*, 12: 31-36 (2013); and Crompton et al., *Cell Stem Cell*, 12: 6-8 (2013).

The pluripotent cells may have a stem cell phenotype including (i) the ability to self-renew and (ii) pluripotency. For example, the pluripotent cells, e.g., iPSCs may be morphologically indistinguishable from embryonic stem cells (ESCs). For example, the pluripotent cells, e.g., iPSCs may have any one or more of a round shape, large nucleolus and small volume of cytoplasm. Alternatively or additionally, the pluripotent cells, e.g., iPSCs may be any one or more of mitotically active, actively self-renewing, proliferating, and dividing. Alternatively or additionally, the pluripotent cells, e.g., iPSCs, may express any one or more of a variety of pluripotency-associated genes. Pluripotency-associated genes may include, but are not limited to, Oct-3/4, Sox2, Nanog, GDF3, REX1, FGF4, ESG1, DPPA2, DPPA4, hTERT and SSEA1. Alternatively or additionally, the pluripotent cells, e.g., iPSCs, may express any one or more of a variety of pluripotency-associated markers. For example, human iPSCs may express any one or more of the markers E-Cadherin, Cbx2, CD9, FGF-4, FGF-5, OCT4, SOX2, SSEA-3, SSEA-4, TRA-1-60, TRA-1-81, TRA-2-49/6E, NANOG, and others. Mouse iPSCs may express the marker SSEA-1.

In embodiments, the inventive method of preparing CD34+CD43+ HPC in vitro comprises culturing source cells in a vessel. The vessel may be a 2D or a 3D vessel. Examples of suitable 2D vessels for culturing source cells include any petri dish or culture dish regularly used in the laboratory for culturing cells. The culturing vessel may be coated with a suitable culturing medium, for example an extracellular medium for the attachment and/or differentiation of cultured cells. An example of a suitable medium for use in the inventive method is MATRIGEL membrane matrix (BD Biosciences, Franklin Lakes, NJ).

Preferably, the vessel is suitable for 3-Dimensional (3D) culture. Without being bound to a particular theory or mechanism, it is believed that 3D culture may be more effective for providing a scaffold for cell differentiation than two dimensional (2D) culture. Suitable 3D culture systems may include, for example, a hanging drop 3D culture, e.g., hanging drop plates, a 3D microwell culture, e.g., ultra-low attachment multiwell plates, a 3D culture on a hydrophobic surface, a rotational culture, a static 3D suspension culture, or a bioreactor. Hanging drop plates are commercially available such as, for example, the PERFECTA3D hanging drop plate, available from Biospherix, Parish, NY Ultra-low attachment multiwell plates are also commercially available such as, for example, AGGREWELL ultra-low attachment, multi-well plate, available from Stemcell Technologies, Vancouver, Canada.

In an embodiment, the method comprises collecting the source cells from the vessel and preparing a single cell suspension of source cells. An example of a suitable vessel for preparing a single cell suspension is a glass or plastic tube. The volume of a suitable tube may be any volume, for example, 10 mL, 20 mL, 30 mL, 40 mL, 50 mL, 60 mL, 70 mL, 80 mL, 90 mL, and/or 100 mL.

In an embodiment, the inventive method comprises culturing the single cell suspension in a first 3D culture and forming embryoid bodies (EBs) from the source cells in the first 3D culture. In embodiments, culturing the single cell suspension in a first 3D culture and forming EBs from the source cells in the first 3D culture may comprise reaggregating the single cell suspension by microcentrifugation.

Embryoid bodies are three-dimensional spheroidal aggregates that spontaneously generate from undifferentiated source cells, e.g., iPSC. EBs may be formed by hemophilic binding of the cell adhesion molecule E-cadherin, which is expressed on undifferentiated ESC and iPSC. When undifferentiated iPSC aggregate into EBs, the EBs have the potential ability to differentiate toward all three germ layers (endoderm, mesoderm, and ectoderm). Without specific culture conditions, it may take about two weeks for EBs to differentiate toward any of the three germ layers, and the differentiation process is performed in a random pattern. For example, EBs generated from human iPSC in floating culture after eight days and then subjected to adhesion culture for an additional eight days without the use of cytokines. The cells from those EBs were immunostained with β-tubulin (an endoderm marker), α-SMA (a mesoderm marker), and AFP (an endoderm marker). The cells were positive for each marker, showing that the EBs derived from iPSC can differentiate to the three germ layers spontaneously (see Tamaoki et al., *J. Dent. Res.*, 89(8): 773-778 (2010)).

EBs that are formed from undifferentiated iPSC overnight in specific culture conditions, as disclosed herein, may show typical pluripotent markers, such as the markers noted above, e.g., any one or more of E-Cadherin, Cbx2, CD9, FGF-4, FGF-5, SOX2, SSEA-3, SSEA-4, TRA-1-60, TRA-1-81, TRA-2-49/6E, and/or NANOG, when they first form, but these EBs may start to lose the pluripotent markers within several days after forming, as the EBs begin to differentiate towards distinct lineages. Therefore, growth factors, cytokines, and specific culture conditions, such as the hMSC culture condition disclosed herein, may be used to guide or boost the differentiation of the EBs toward the hematopoietic lineage, which is formed through the mesoderm lineage. EB cells that have differentiated toward hematopoietic lineage can be identified by major hematopoietic lineage markers, such as, for example, any one or more of CD34, CD43, CD45, CD41, C235, and CD90. In an embodiment of the invention, the EBs comprise differentiated cells. The 3D culture used to culture the EBs overnight may be any 3D culture described herein, such as an ultra-low attachment multiwell plate or a bioreactor.

In embodiments, the inventive method further comprises collecting the EBs, mixing the EBs with mesoderm lineage cells (MLC), and preparing a single cell suspension comprising EBs and MLC. The single cell suspension may include HPC differentiation medium such as, for example, αMEM containing 20% FCS (Macopharma, Mouvaux, France) or PLTMAX αMEM containing 10% human platelet lysate (Sigma). The MLC may be used to guide or boost the EBs towards the mesoderm lineage such that the EBs can thus differentiate toward the hematopoietic lineage. MLC may include, for example, the following types of human or non-human cells: bone marrow stromal cells, mesenchymal stem cells, embryonic fibroblast cells, stromal cells derived from cranial dental pulp, and primitive mesodermal cells. Markers of such MLC include, for example, any one or more of KDR, PDFGR, APLNR, T, MIXL, FOXF1, GATA2, and RUNX1. Any cell that is on the differentiation pathway between human iPSC to HPC may be a MLC suitable for use in the inventive method. The MLC may include, for example, any one or more of an iPS-derived primitive mesoderm cell, an iPS-derived hemangioblast cell, an iPSC-derived hematoendothelial cell, an iPS-derived stromal cell, and an iPS-derived mesenchymal stem cell, among others.

In embodiments, the inventive method further comprises co-culturing the EBs with MLC in the single cell suspension in a second 3D culture and forming hematopoietic spheroids (e.g., lobes) in the second 3D culture. As used herein, the term "lobes" or "hematopoietic spheroids" means the spheroidal structures that form when either (1) EBs are mixed with MLC, and the EB/MLC mixture spontaneously aggregates into spheroids or (2) undifferentiated source cells, e.g., iPSCs, the numbers of which have expanded in a stirred suspension bioreactor, and the undifferentiated source cells and the MLC spontaneously aggregate into spheroids without forming EBs. As described herein, the term "hematopoietic spheroids" encompasses both spheroidal EB/MLC-derived aggregates, and spheroidal undifferentiated source cell/MLC-derived aggregates. The first and second 3D cultures suitable for use in the inventive method may comprise any suitable 3D culture, for example, a hanging drop 3D culture, a 3D microwell culture, a 3D culture on a hydrophobic surface, a rotational culture, a static 3D suspension culture, or a bioreactor, as described herein with respect to other aspects of the invention.

In embodiments, the inventive method further comprises collecting the hematopoietic spheroids from the second 3D culture and culturing the hematopoietic spheroids in a third 3D culture. The hematopoietic spheroids may be transferred to a third 3D culture by, for example, collecting the hematopoietic spheroids in a tube and centrifuging, removing the supernatant, then adding the hematopoietic spheroids to any 3D culture described herein, such as a hanging drop culture plate or a bioreactor with fresh HPC differentiation medium. The hematopoietic spheroids may be cultured in the third 3D culture for a period of from about 1 to about 13 days. During this period, the individual cells derived from the cultured hematopoietic spheroids desirably differentiate into cells of hematopoietic lineage cells, such as CD34+CD43+ hematopoietic progenitor cells.

In embodiments, the inventive method further comprises harvesting CD34+CD43+ hematopoietic progenitor cells from the hematopoietic spheroids. Harvesting the hematopoietic spheroids may encompass, for example, collecting the hematopoietic spheroids from the third 3D culture and gently breaking the hematopoietic spheroids apart with trypsin, for example, and/or by gently pipetting, such that the individual cells become separated from the hematopoietic spheroids and, thus may be subjected to, for example, flow cytometry and analysis, and/or treatment.

In an embodiment, culturing may be carried out in xeno-free medium. As used herein the term "xeno-free" refers to an absence of direct or indirect exposure to non-human animal components. Advantages of xeno-free medium include the absence of potential contaminants and improved consistency in both performance and quality of the culture medium. In this regard, culturing the hematopoietic spheroids in a first, second, and/or third 3D culture preferably takes place in xeno-free medium. In a preferred embodiment, the xeno-free medium comprises human platelet lysate.

In an embodiment, the inventive method is carried out in the absence of one or more exogenous cytokines. In other embodiments, the inventive method may be carried out in the presence of one or more exogenous cytokines. In this regard, any one of, or all of (i) culturing source cells in a vessel; (ii) collecting the source cells from the vessel and preparing a single cell suspension of source cells; (iii) culturing the single cell suspension in a first three-dimensional (3D) culture and forming EBs from the source cells in the first 3D culture; (iv) collecting the EBs, mixing the EBs with MLC, and preparing a single cell suspension comprising EBs and MLC; (v) co-culturing the EBs and MLC in the single cell suspension in a second 3D culture and forming hematopoietic spheroids in the second 3D culture; (vi) collecting the hematopoietic spheroids from the second 3D culture and culturing the hematopoietic spheroids in a third 3D culture; and (vii) harvesting CD34+CD43+ hematopoietic progenitor cells from the hematopoietic spheroids may be carried out in the presence or absence of one or more exogenous cytokines. The one or more exogenous cytokines may comprise one or more of Fms-related tyrosine Kinase 3 (FLT3L), thrombopoietin (TPO), vascular endothelial growth factor (VEGF), platelet-derived growth factor (PDGF), fibroblast growth factor basic (bFGF), bone morphogenic protein 4 (BMP4), interleukin-3 (IL-3), interleukin-6 (IL-6), stem cell factor (SCF), granulocyte-colony stimulating factor (G-CSF), granulocyte macrophage-colony stimulating factor (GM-CSF), macrophage-colony stimulating factor (M-CSF), interferon alpha (IFNα), interferon beta (IFNβ), interferon gamma (IFNγ), tumor necrosis factor alpha (TNFα), tumor necrosis factor beta (TNFβ), WNT pathway activator CHIR99021, ascorbic acid, and mono-thioglycerol.

Additional advantages provided by the inventive method may be carried out without forming EBs. In an embodiment, the inventive method may comprise forming source cells into spheroids in a bioreactor by culturing the source cells in suspension in the bioreactor. Suitable source cells may be any source cells described herein, with respect to other aspects of the invention, for example, hiPSC, hESC, nuclear transfer-derived human embryonic stem cells, EPS cells, lineage-reprogrammed cells, transdifferentiated cells, dedifferentiated cells, or transdetermined cells. It was found that certain source cells, such as the source cells provided herein, for example, undifferentiated iPSC, may spontaneously aggregate into spheroids directly in a bioreactor. Advantageously, it was found that the spheroids formed directly in bioreactors may be approximately the same size as spheroids formed in other 3D culture systems, including e.g., ultra-low attachment microwell plates. In an embodiment, the inventive method may comprise forming source cells into spheroids directly in a bioreactor without forming EBs by culturing the source cells in suspension in the bioreactor in xeno-free medium. The spheroids may comprise undifferentiated source cells, e.g., undifferentiated iPSC.

In an embodiment, the inventive method further comprises collecting the spheroids from the bioreactor and mixing the spheroids with MLC. Suitable MLC includes any of the MLC described herein with respect to other aspects of the invention, for example, human mesenchymal stem cells.

In an embodiment, the inventive method may further comprise co-culturing the spheroids with the MLC in a first 3D culture and forming hematopoietic spheroids in the first 3D culture. Co-culturing may encompass breaking up the spheroids into individual cells and mixing the individual cells in a cell suspension with suitable MLC and suitable differentiation medium, and then adding the cell suspension to any suitable 3D culture, such that hematopoietic spheroids form in the 3D culture. Any 3D culture described herein is suitable for use as a first 3D culture.

In an embodiment, the inventive method further comprises collecting the hematopoietic spheroids from the first 3D culture and culturing the hematopoietic spheroids in a second 3D culture. Any 3D culture described herein with respect to other aspects of the invention is suitable for use as a second 3D culture.

In an embodiment, the inventive method further comprises harvesting CD34+CD43+ hematopoietic progenitor cells from the hematopoietic spheroids. Harvesting CD34+CD43+ hematopoietic progenitor cells may encompass, for example, collecting the hematopoietic spheroids from the third 3D culture and gently breaking the hematopoietic spheroids apart with trypsin, for example, or by gently pipetting, such that the individual CD34+CD43+ hematopoietic progenitor cells may be subjected to flow cytometry and analysis and/or treatment.

In an embodiment, the inventive method may be carried out in the presence or absence of one or more exogenous cytokines. In this regard, any one of, or all of (i) forming source cells into spheroids in a bioreactor by culturing the source cells in suspension in the bioreactor; (ii) collecting the spheroids from the bioreactor and mixing the spheroids with mesoderm lineage cells (MLC); (iii) co-culturing the spheroids with the MLC in a first 3D culture and forming hematopoietic spheroids in the first 3D culture; (iv) collecting the hematopoietic spheroids from the first 3D culture and culturing the hematopoietic spheroids in a second 3D culture; and (v) harvesting CD34+CD43+ hematopoietic progenitor cells from the hematopoietic spheroids may be carried out in the presence or absence of one or more exogenous cytokines. Suitable exogenous cytokines include any of the exogenous cytokines that are described herein with respect to other aspects of the invention.

In additional embodiments, the inventive method may comprise culturing the source cells in xeno-free medium.

In a further embodiment, the source cells may be induced pluripotent stem cells (iPSC), and the method further comprises reprogramming human T-cells to produce the iPSC.

In an embodiment, the inventive method may further comprise differentiating the CD34+CD43+ hematopoietic progenitor cells to CD4+CD8+ cells. HPC can differentiate into the T cell lineage by inducing Notch signaling. Notch signaling can be induced in a variety of ways, e.g., seeding the cells onto OP9-DL1 mouse stromal cells; adding Delta like ligand 4 (DLL4), a protein that is encoded by the DLL4 gene; or adding antibodies to notch receptors in the HPC to the CD34+CD43+ HPC-containing medium. In an embodiment, differentiating the CD34+CD43+ hematopoietic progenitor cells may comprise harvesting the CD34+CD43+ expressing HPC and seeding the cells onto OP9-DL1 mouse stromal cells with T cell differentiation medium, and converting to new OP9-DL1 dishes after 3 days, and again between about day 16 to day 30, every 7 days. After about day 30, floating cells may be passaged onto a new OP9-DL1 dish every 5 days. According to an embodiment of the invention, the CD34+CD43+ HPCs can thus be differentiated to $CD4^+$, $CD8^+$, $CD3^+$, $CD7^+$ T cell lineage cells by approximately day 41. Major hematopoietic lineage markers found on different types of T cells include for example: $CD4^+$ (helper T cells and regulatory T cells), $CD8^+$ (cytotoxic T cells), $CD3^+$ (all T cells), and $CD7^+$ (differentiation marker that identifies multiple CD8 T cell effector subsets).

An embodiment of the invention also provides an isolated or purified cell prepared by the inventive method. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than about 60%, about 70% or about 80%, or can be about 100%.

An embodiment of the invention may further provide an isolated or purified population of cells comprising at least one cell prepared according to any of the methods described herein. The population of cells can be a heterogeneous population comprising the inventive cells in addition to a cell other than the inventive cells. The population of cells can be a substantially homogeneous population, in which the population comprises mainly of (e.g., consisting essentially of) inventive cells. In an embodiment of the invention, about 1% to about 100%, for example, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, or a range defined by any two of the foregoing values, of the population of cells comprises inventive cells.

The inventive populations of cells can be formulated into a composition, such as a pharmaceutical composition. In this regard, an embodiment of the invention provides a pharmaceutical composition comprising any of the inventive populations of cells described herein and a pharmaceutically acceptable carrier. The inventive pharmaceutical composition can comprise an inventive population of cells in combination with another pharmaceutically active agent(s) or drug(s), such as a chemotherapeutic agent, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive population of cells under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive population of cells, as well as by the particular method used to administer the inventive population of cells. Accordingly, there are a variety of suitable formulations of the pharmaceutical composition of the invention. Suitable formulations may include any of those for oral, parenteral, subcutaneous, intratumoral, intravenous, intramuscular, intraarterial, intrathecal, or interperitoneal administration. More than one route can be used to administer the inventive population of cells, and in certain instances, a particular route can provide a more immediate and more effective response than another route.

Preferably, the inventive population of cells is administered by injection, e.g., intravenously. When the inventive population of cells is to be administered, the pharmaceutically acceptable carrier for cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumin.

For purposes of the invention, the amount or dose of the inventive population of cells or pharmaceutical composition administered (e.g., numbers of cells when the inventive population of cells is administered) should be sufficient to effect, e.g., a therapeutic or prophylactic response, in the mammal over a reasonable time frame. For example, the dose of the inventive population of cells or pharmaceutical composition should be sufficient to treat or prevent a condition in a period of from about 2 hours or longer, e.g., 12 to 24 or more hours, from the time of administration. In certain embodiments, the time period could be even longer. The dose will be determined by the efficacy of the particular inventive population of cells or pharmaceutical composition administered and the condition of the mammal, as well as the body weight of the mammal to be treated.

Many assays for determining an administered dose are known in the art. For purposes of the invention, an assay, which comprises comparing the extent to which target cells are lysed upon administration of a given dose of such cells to a mammal among a set of mammals of which is each given a different dose of the cells, could be used to determine a starting dose to be administered to a mammal. The extent to which target cells are lysed upon administration of a certain dose can be assayed by methods known in the art.

The dose of the inventive population of cells or pharmaceutical composition also will be determined by the existence, nature and extent of any adverse side effects that might accompany the administration of a particular inventive population of cells or pharmaceutical composition. Typically, the attending physician will decide the dosage of the population of cells or pharmaceutical composition with which to treat each individual mammal, taking into consideration a variety of factors, such as age, body weight, general health, diet, sex, inventive population of cells or pharmaceutical composition to be administered, route of administration, and the severity of the condition being treated.

Any suitable number of inventive cells can be administered to a mammal. While a single inventive cell is theoretically capable of expanding and providing a therapeutic benefit, it is preferable to administer about $10^2$ or more, e.g., about $10^3$ or more, about $10^4$ or more, about $10^5$ or more, about $10^8$ or more, T cells of the invention. Alternatively, or additionally about $10^{12}$ or less, e.g., about $10^{11}$ or less, about $10^9$ or less, about $10^7$ or less, or about $10^5$ or less, cells of the invention can be administered to a mammal. The number of cells of the invention can be administered to a mammal in an amount bounded by any two of the above endpoints, e.g., about $10^2$ to about $10^5$, about $10^3$ to about $10^7$, about $10^3$ to about $10^9$, or about $10^5$ to about $10^{10}$. For example, about $10^7$ to about $10^8$ CD34+CD43+ cells may be administered.

In an embodiment, the invention provides a method of treating or preventing a condition in a mammal, the method comprising: preparing HPC in vitro and administering the HPC to the mammal in an amount effective to treat or prevent the condition in the mammal. In an embodiment, the method may comprise preparing HPC in vitro by any of the inventive methods disclosed herein and further differentiating the HPC into any one or more of the following hematopoietic lineage cells: erythroids, granulocytes, megakaryocytes, dendritic cells, platelet cells, B cells, T cells, natural killer (NK) cells, and natural killer T (NKT) cells; and administering the any one or more of the hematopoietic lineage cells or population of cells to the mammal in an amount effective to treat or prevent the condition in the mammal. In an embodiment of the invention, the condition is a cancer, an immunodeficiency, an autoimmune condition, an infection, or a blood condition.

In an embodiment, the invention provides a method of treating or preventing a condition in a mammal, the method comprising administering the CD34+CD43+ HPC or a population of CD34+CD43+ HPCs prepared according to the inventive methods to the mammal in an amount effective to treat or prevent the condition in the mammal.

The cancer may be any cancer, including, for example, any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

The immunodeficiency may be any condition in which the body's ability to defend itself against outside pathogens is disrupted. The immunodeficiency may be any condition in which a patient's immune system is compromised and in need of reconstitution after immunodeployment due to irradiation or chemotherapy. Immunodeficiency may include, for example, a depleted adaptive immune system in the elderly population. Without being bound to a particular theory or mechanism, it is believed that the cells of the invention may be useful for the treatment of both primary and secondary immunodeficiencies. Examples of immunodeficiencies which may be treated or prevented include, but are not limited to X-linked agammaglobulinemia (XLA), variable immunodeficiency (CVID), severe combined immunodeficiency (SCID), AIDS, and hepatitis.

The autoimmune condition may be any condition in which the body's immune system attacks healthy cells. Without being bound to a particular theory or mechanism, it is believed that the cells prepared by the inventive methods may be useful for the treatment of autoimmune conditions. Examples of autoimmune conditions which may be treated or prevented include, but are not limited to, rheumatoid arthritis, lupus, type 1 diabetes, multiple sclerosis, celiac disease, temporal arteritis, vasculitis, alopecia areata, ankylosing spondylitis, Sjögren's syndrome, and polymyalgia rheumatic.

The infection may be an infectious condition, for example, a viral condition, a bacterial condition, a fungal condition, or a protozoan condition.

For purposes herein, "viral condition" means a condition that can be transmitted from person to person or from organism to organism, and is caused by a virus. In an embodiment of the invention, the viral condition is caused by a virus selected from the group consisting of herpes viruses, pox viruses, hepadnaviruses, papilloma viruses, adenoviruses, coronoviruses, orthomyxoviruses, paramyxoviruses, flaviviruses, and caliciviruses. For example, the viral condition may be caused by a virus selected from the group consisting of respiratory syncytial virus (RSV), influenza virus, herpes simplex virus, Epstein-Barr virus, varicella virus, cytomegalovirus, hepatitis A virus, hepatitis B virus, hepatitis C virus, human immunodeficiency virus (HIV), human T-lymphotropic virus, calicivirus, adenovirus, and Arena virus.

The viral condition may be, for example, influenza, pneumonia, herpes, hepatitis, hepatitis A, hepatitis B, hepatitis C, chronic fatigue syndrome, sudden acute respiratory syndrome (SARS), gastroenteritis, enteritis, carditis, encephalitis, bronchiolitis, respiratory papillomatosis, meningitis, HIV/AIDS, and mononucleosis.

The blood condition may be any non-cancerous condition that affects the blood. The blood condition may be, for example, cytopenia (e.g., anemia, leukopenia, and neutropenia), bleeding disorders such as hemophilia, and blood clots.

The term "mammal" as used herein refers to any mammal, including, but not limited to, mice, hamsters, rats, rabbits, cats, dogs, cows, pigs, horses, monkeys, apes, and humans. Preferably, the mammal is a human.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition being treated or prevented. For example, treatment or prevention can include promoting the regression of a tumor. Also, for purposes herein, "prevention" can encompass preventing the recurrence of the condition, delaying the onset of the condition, or a symptom or condition thereof.

The following examples further illustrate the invention but, of course, should not be construed as in any way limiting its scope.

EXAMPLES

The materials and methods employed in Examples 1-6 are provided below.

Culturing Human iPSC

Figure 4:
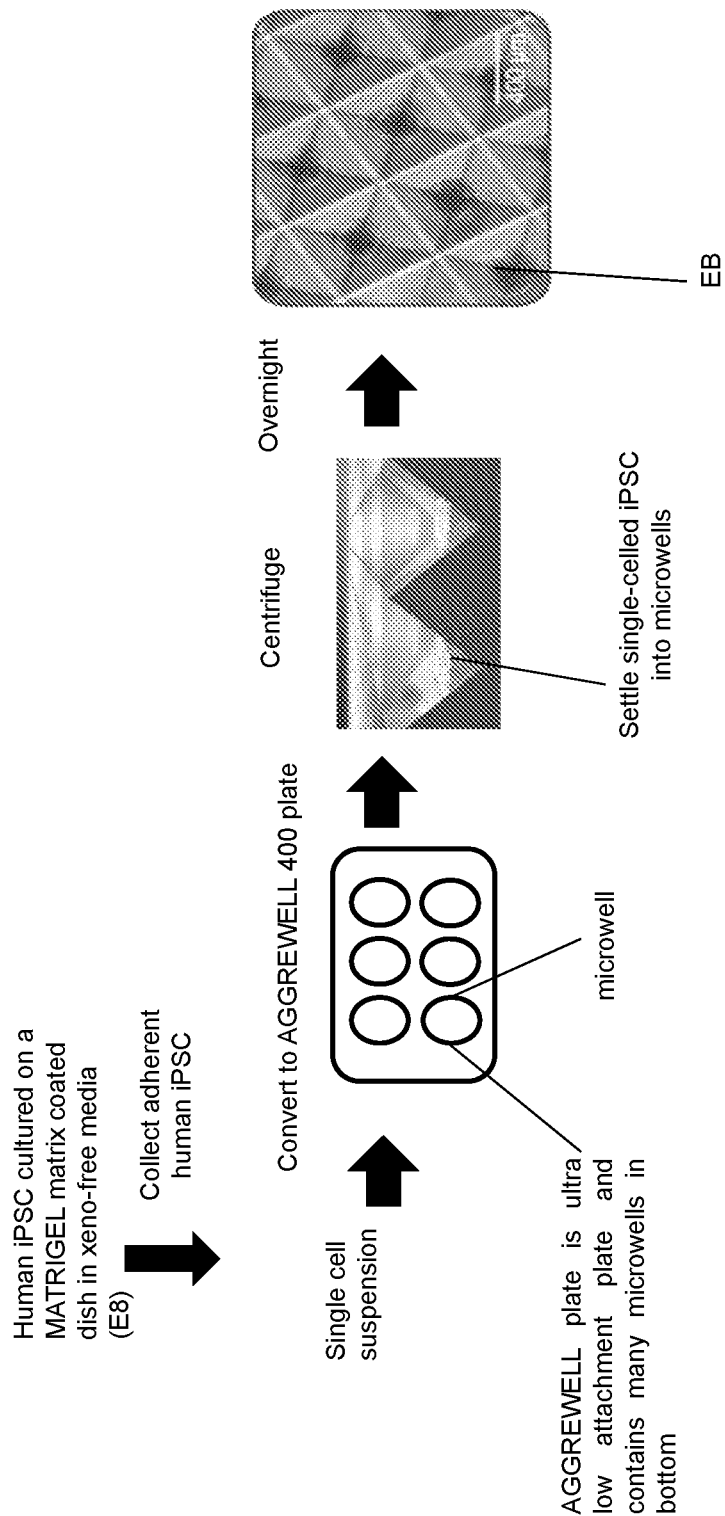
FIG. 4 is a schematic showing a method of culturing human iPSC in xeno-free media, preparing a single cell suspension, adding the suspension to an AGGREWELL 400 plate, and settling single-celled iPSC into microwells by centrifugation. Culturing iPSC overnight in microwells results in the formation of small EBs according to an embodiment of the invention.

Human iPSC were cultured on MATRIGEL membrane matrix (BD Biosciences, Franklin Lakes, NJ) coated dishes in ESSENTIAL 8 ("E8") xeno-free media (Invitrogen, Waltham, MA), as shown in FIG. 4. The media was changed daily. iPSC were routinely passaged as small clumps/single cells using PBS/EDTA medium (0.5 mM EDTA in PBS) with the split ratio of 1:6 to 1:10 every 3 to 4 days after reaching 65% to 80% confluence.

Passaging the cells involved washing cells twice with PBS/EDTA medium, and then incubating with PBS/EDTA for 4-5 minutes at 37° C. PBS/EDTA was removed and E8 supplemented with 10 µM of STEMOLECULE Y27632 ROCK inhibitor (Stemgent, Lexington, MA) was added to break iPSC colonies into small clumps or single cells by gently pipetting. Cells were added to new MATRIGEL coated dishes and cultured in E8 supplemented with 10 µM of Y-27632 2HCl ROCK inhibitor (Sigma, St. Louis, MO) overnight. The following day, the medium was changed to E8 medium without ROCK inhibitor.

Generation of Embryoid Bodies (EBs) from Human iPSC

Figure 5:
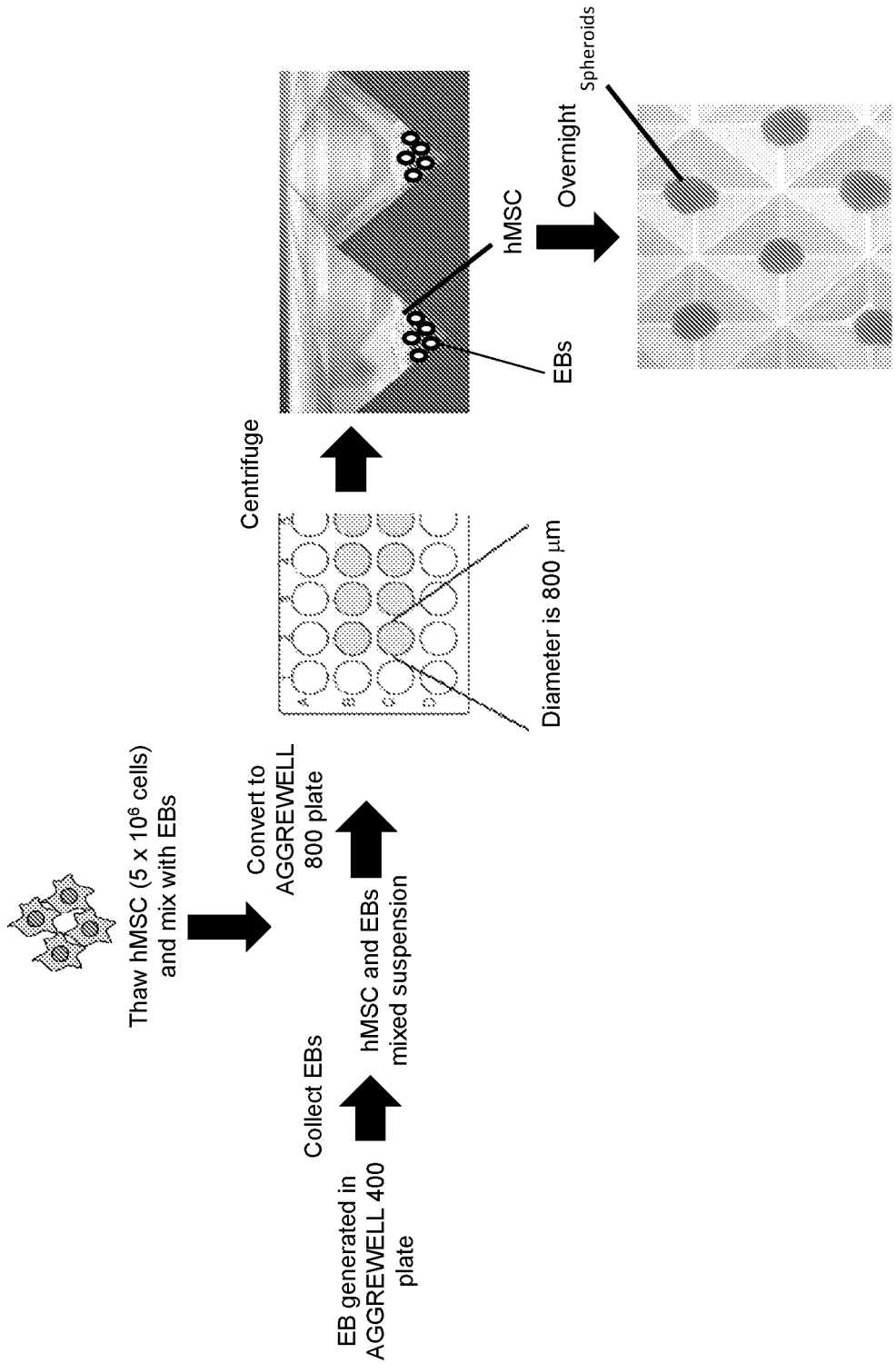
FIG. 5 is a schematic showing a method of mixing hMSCs and EBs in a mixed suspension and adding the suspension to an AGGREWELL 800 plate which results in the formation of hematopoietic spheroids according to an embodiment of the invention.

AGGREWELL (Stemcell Technologies Inc., Hamilton, NC) rinsing solution (1 mL) was added to each AGGREWELL 400Ex well in an AGGREWELL 400Ex plate and centrifuged for 5 minutes at 2000 g. The rinsing solution was removed and each well was washed once with EBS media (E8 medium supplemented with 10 µM ROCK inhibitor and 4 mg/mL polyvinyl alcohol).

iPSC were washed twice with PBS/EDTA and incubated with PBS/EDTA for 4-5 minutes at 37° C. The PBS/EDTA was removed and EBS media was added to collect iPSC as single cells by gently pipetting. A single-cell suspension was prepared ($0.8 \times 10^5$ cells/mL), as shown in FIG. 4, and 5 mL were added to each AGGREWELL 400Ex well. After the cells were added, the cell mixture was pipetted gently several times to distribute the cells evenly throughout the well. This pipetting was performed immediately after adding the cell mixture. The AGGREWELL 400Ex plate was centrifuged at 100 g for 3 minutes to capture the cells into the microwells (FIG. 4). The AGGREWELL 400Ex plate was examined under a microscope to verify that cells were evenly distributed among the microwells. The cells were incubated at 37° C. overnight, after which EBs had formed (FIG. 4).

Generation of Hematopoietic Spheroids by Mixing EBs and hMSC

AGGREWELL rinsing solution (0.5 mL) was added to each well in an AGGREWELL 800 plate and centrifuged for 5 minutes (2000 g). The rinsing solution was removed and each well was washed once with MULTIPL αMEM HPC differentiation medium (αMEM containing 20% FCS (Macopharma, Mouvaux, France) or PLTMAX αMEM containing 10% human platelet lysate (Sigma). Small EBs were collected from the AGGREWELL 400Ex plate by gently pipetting and mixed with bone marrow derived hMSC ($5 \times 10^6$ cells) (FIG. 5) to make an EB/hMSC cell suspension with HPC differentiation medium, and then added to the AGGREWELL 800 plates, as shown in FIG. 5. The bone marrow derived hMSC was contained in a previously frozen 50 mL tube ($5 \times 10^6$ cells/tube) that was thawed to mix with EBs collected from four AGGREWELL 400Ex wells. One AGGREWELL 400Ex well contained 4000-4500 EBs. It was found that a ratio of hMSC to iPSC is 1:1 is suitable, because too many iPSC or too many hMSC can impair the generation of HPC.

After making the EBs/hMSC cell suspension with HPC differentiation medium in a 50 mL tube, the suspension was added to eight AGGREWELL 800 wells (2 mL of cell suspension were put into each well), as shown in FIG. 5. The wells were centrifuged at 800 rpm for 3 minutes immediately to settle the hMSC and EBs into the microwells of the AGGREWELL 800 plate. The EBs and hMSC were cultured in the microwells overnight to form hematopoietic spheroids (FIG. 5).

Figure 6:
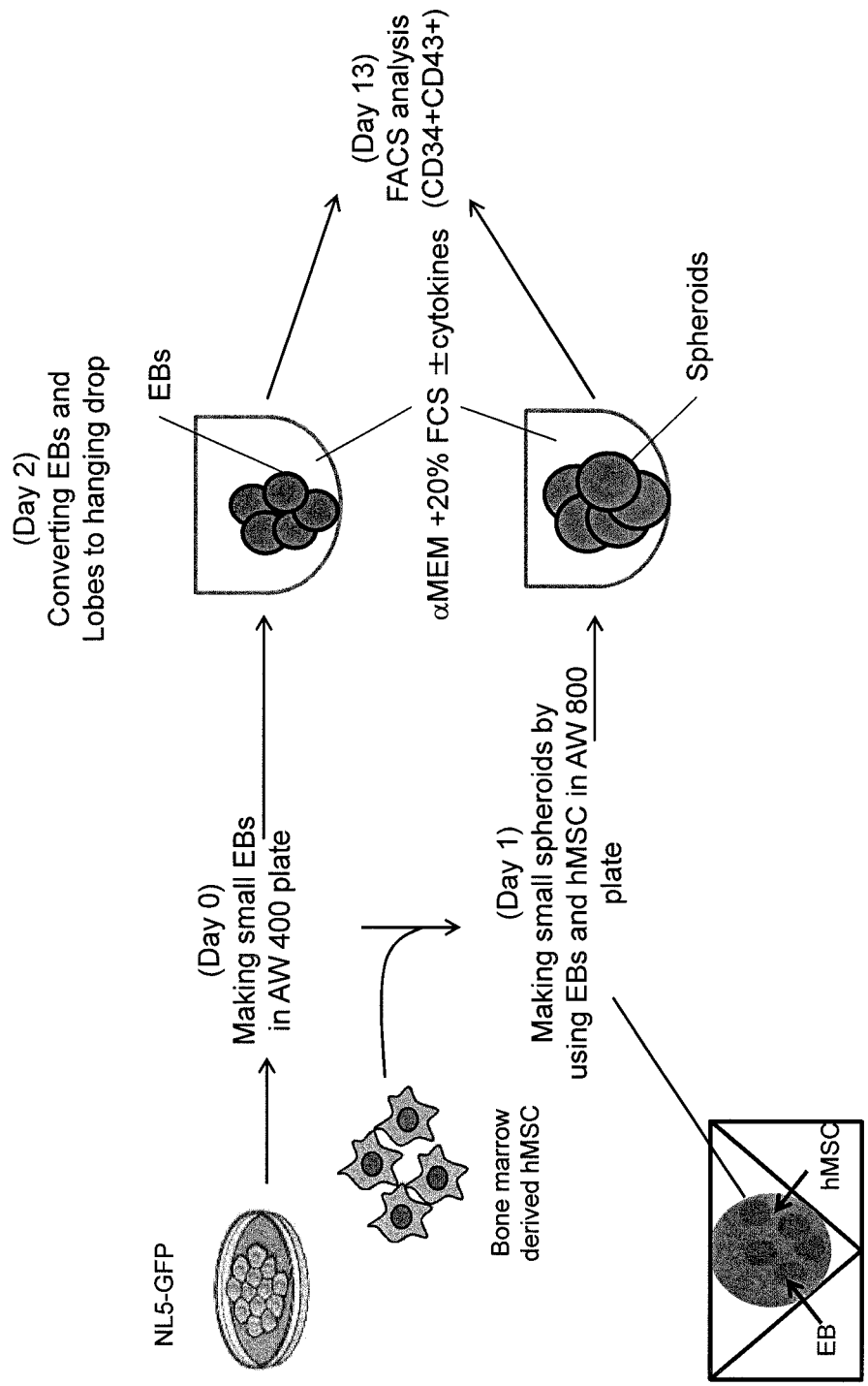
FIG. 6 is a schematic showing a method of producing CD34+CD43+ cells by culturing EBs and hematopoietic spheroids with and without cytokines in a 3D hanging drop culture condition according to an embodiment of the invention.

The following day, the hematopoietic spheroids were collected in a 50 mL tube and centrifuged at 800 rpm for 3 minutes. The supernatant was removed and the hematopoietic spheroids were added to a PERFECTA 3D hanging drop culture plate (Sigma) as shown in FIG. 6, or to a disposable bioreactor with fresh HPC differentiation medium. EBs (without hMSC) were also added to a PERFECTA 3D hanging drop culture plate on Day 2 (FIG. 6).

Culturing of Hematopoietic Spheroids in a Bioreactor

The ABLE Bioreactor Magnetic Stir System 3D magnetic stir and disposable bioreactor (Stemgent) was used to culture 2000-2400 hematopoietic spheroids in 30 mL of differentiation medium. The stir speed for culturing hematopoietic spheroids was set as 60 rpm. The medium was changed every 2-3 days.

Dissociation of Hematopoietic Spheroids

On day 13, hematopoietic spheroids were collected from the bioreactor into a 50 mL tube, centrifuged at 1200 rpm for 5 minutes, and the supernatant was removed. HBSS (Hank's Balanced Salt Solution) containing 10% LIBERASE TH (Sigma) and 10% DNase I (Sigma) were added, and then the hematopoietic spheroids were incubated in a 37° C. water bath for 20-25 minutes. Hematopoietic spheroids were broken by pipetting several times and then centrifuged at 1200 rpm for 5 minutes. The supernatant was then removed. Trypsin (0.25%) containing 10% DNase I (Sigma) was added and the broken hematopoietic spheroids were incubated in a 37° C. water bath for 20-25 minutes. Broken hematopoietic spheroids were made into single cells by pipetting and adding αMEM+20% FCS to block trypsin treatment, then centrifuging at 1200 rpm for 5 minutes. The supernatant was then removed. For flow cytometric analysis, PBS was added to make a single-cell suspension (FIG. 6).

Differentiation of CD34+CD43+ HPCs Toward T Cell Lineage

On day 13, the hematopoietic spheroids were harvested and dissociated as described above, then seeded onto OP9-DL1 mouse stromal cells with T cell differentiation medium (αMEM supplemented 20% FCS, 10 ng/mL Flt3l (R&D Systems, Minneapolis, MN), 10 ng/mL IL7 (R&D), and 10 ng/mL SCF (R&D)) (FIG. 8A). After 3 days (on day 16), the floating cells were harvested by gently pipetting and the cells were then added to a new OP9-DL1 dish with T cell differentiation medium. From day 16 to day 30, floating cells were re-seeded onto a new OP9-DL1 dish with T cell differentiation medium every 7 days. After day 30, floating cells were passaged onto a new OP9-DLL dish every 5 days. Using this process, CD34+CD43+ HPCs can be differentiated to CD4+CD8+ immature T cells by approximately day 40 (FIG. 8A).

iPSC Expansion in Stirred Suspension Bioreactors iPSC were cultured on MATRIGEL plates until 65-80% confluence. iPSC were washed twice with PBS/EDTA medium, and then incubated with PBS/EDTA for 4-5 minutes at 37° C. The PBS/EDTA was then removed. E8 medium supplemented with 10 μM ROCK inhibitor was added and the mixture was gently pipetted to produce iPSC as single cells. The cells were added to a 50 mL tube and E8 supplemented with 10 μM ROCK inhibitor was added to make a cell suspension ($1.5 \times 10^5$/mL). iPSC single-cell suspension (30 mL) was added to an ABLE bioreactor magnetic stir system. The following day, the medium was changed to E8 without ROCK inhibitor. At this point, the iPSC cultured in the bioreactor formed spheroid structures. After 2-3 days, the size of spheroid-iPSC had reached the same size as EBs formed in the AGGREWELL 400Ex plate. Spheroid-iPSCs were collected and counted. Spheroid-iPSCs ($1.6 \times 10^4$) were taken to mix with hMSC (one frozen tube of $5 \times 10^6$ cells/tube) in a 50 mL tube. The spheroid-iPSC/hMSC cell suspension was added with HPC differentiation medium to eight AGGREWELL 800 wells for making hematopoietic spheroids (2 mL cell suspension into each AGGREWELL 800 well). The following day, hematopoietic spheroids were collected in a 50 mL tube and centrifuged at 800 rpm for 3 minutes. The supernatant was removed and the hematopoietic spheroids were added to a bioreactor with 30 mL fresh HPC differentiation medium.

Comparative Example 1

This example demonstrates the use of hMSC as feeder cells for growing iPSC in a 2D culture and then adding the iPSC to an OP9-DL1 2D system.

Experiments using hMSC as feeder cells in a 2-dimensional (2D) system were performed (FIG. 1A). In the experiments, hMSC were used as feeder cells, and iPSC were grown on the hMSC in a 2D culture to produce differentiated HPC. The differentiated iPSC were then transferred to an OP9-DL1 system on day 13 for differentiation into CD34+CD43+ cells, as shown in FIG. 1A. The cells were tested for CD4+ and CD8+ on day 35. OP9-DL1 cells are a bone-marrow-derived stromal cell line that ectopically expresses cytokines involved in differentiation to hematopoietic cells, including e.g., one or more of Fms-related tyrosine kinase 3 ligand (FLT3LG), interleukin 7 (IL-7), and Stem cell factor (SCF), as shown in FIG. 1A. However, it was found that the success rate for the production of CD34+CD43+ using this system is less than 10% and is not replicable. It was additionally found that CD34+CD43+ cells produced by the hMSC feeder cell co-culturing system in a 2D monolayer do not successfully produce double positive T cells, as shown in FIGS. 1B-1C. One possible reason for the poor results of using hMSC in place of OP9, was that the dome-shaped colonies (FIG. 2A) and sac-like structures (FIG. 2B) formed during differentiation on OP9 did not form when using hMSC as feeder cells in place of OP9. As shown in FIGS. 2A-2B, the dome-shaped colonies formed on OP9 are flattened when using hMSC in place of OP9 (FIG. 2A, Day 1, "flattened colony"). Similarly, the dome-shaped colonies formed on day 1 on OP9 develop into sac-like structures by day 13 (FIG. 2B). However, such colonies did not develop when using hMSC in place of OP9 (FIG. 2B, Day 13, "colonies cannot be developed"). Therefore, the cell culturing system for differentiation of iPSC towards HPC in a 3D culture was tested, as described below.

Example 1

This example demonstrates that co-culturing iPSC with hMSC can produce CD34+CD43+ cells without the use of cytokines.

Figure 3:
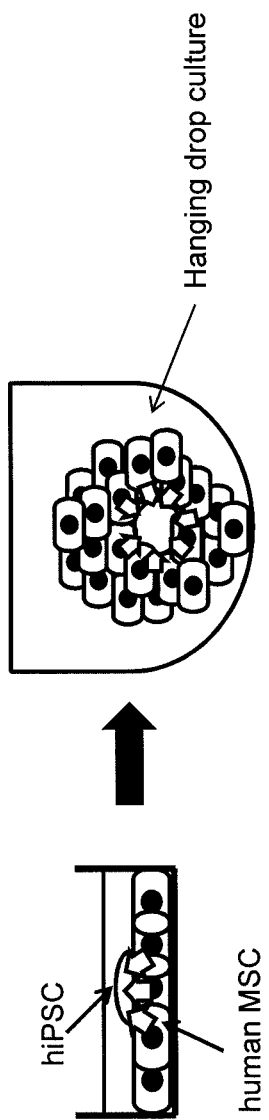
FIG. 3 is a schematic showing a method of using a 3D culture condition for co-culturing human iPSC and human MSC in a hanging drop culture according to an embodiment of the invention.

A 3D hanging drop culture (FIG. 3) was used to promote formation of the sac-like structures that are involved in differentiation of hiPSC into human HPC (shown in FIGS. 2A-2B) and provide a better scaffold for iPSC differentiation.

A single cell suspension from iPSC was cultured on MATRIGEL membrane matrix coated dishes in ESSENTIAL 8 xeno-free media (Gibco, was prepared ($0.8 \times 10^5$ cells/mL), as shown in FIG. 4. The cell suspension (5 mL) was added to each AGGREWELL 400Ex well, and the cell mixture was immediately pipetted gently several times to distribute the cells evenly throughout the wells. The AGGREWELL 400Ex plate was centrifuged at 100 g for 3 minutes to capture the cells into the microwells. The cells were incubated at 37° C. overnight, after which EBs had formed (FIG. 4).

Small EBs were collected from the AGGREWELL 400Ex plate by gently pipetting and mixing with bone marrow derived hMSC ($5 \times 10^6$ cells) (FIG. 5) to make an EBs/hMSC cell suspension with HPC differentiation medium, and then added to AGGREWELL 800 plates, as shown in FIG. 5. One AGGREWELL 400Ex well contains 4000-4500 EBs. The preferred ratio of hMSC to iPSC was 1:1 because it is believed that too many iPSC or too many hMSC can impair the generation of HPC.

After making the EB/hMSC cell suspension with HPC differentiation medium in a 50 mL tube, the suspension was added to eight AGGREWELL 800 wells (2 mL of cell suspension were put into each well). The wells were centrifuged at 800 rpm for 3 minutes immediately to settle the hMSC and EBs into the microwells of the AGGREWELL 800 plate. The EBs and hMSC were cultured in the microwells overnight to form spheroids, as shown in FIG. 5.

The EBs and hematopoietic spheroids were each separately added to PERFECTA 3D hanging drop culture plates with fresh HPC differentiation medium (αMEM+20% FCS±cytokines) as shown in FIG. 6. The EBs and hematopoietic spheroids were disassociated for FACS analysis. On day 13, the cells from the following hanging drop cultures (about 96 hanging drops in each group) underwent FACS analysis: (1) EBs in αMEM HPC differentiation medium+20% FCS with the following added cytokines: BMP4, bFGF, VEGF, IL-3, IL-6, Flt3, TPO, and SCF, (2) EBs in αMEM HPC differentiation medium+20% FCS without added cytokines, (3) hematopoietic spheroids in αMEM HPC differentiation medium+20% FCS with the following added cytokines: BMP4, bFGF, VEGF, IL-3, IL-6, Flt3, TPO, and SCF, and (4) hematopoietic spheroids in αMEM HPC differentiation medium+20% FCS without added cytokines. The FACS results, shown in FIGS. 7A-7E, show that co-culturing the iPSC-derived hematopoietic spheroids can produce CD34+CD43+ cells without the use of cytokines (FIGS. 7C and 7E). As shown in FIGS. 7C and 7E, 15.8% of the cells produced by the hiPSC-derived hematopoietic spheroids produced CD34+CD43+ cells.

Example 2

This example demonstrates that CD34+CD43+ cells derived from hematopoietic spheroids have potency to produce T cell progenitors.

PERFECTA 3D hanging drop cultures were prepared containing either (1) EBs with the cytokines listed in Example 1, (2) EBs without the cytokines, (3) hematopoietic spheroids with the cytokines listed in Example 1, or (4) hematopoietic spheroids without cytokines, as described in Example 1. To evaluate the differentiation potency toward T cell lineage of the CD34+CD43+ cells obtained from the EBs and hematopoietic spheroids, the CD34+CD43+ cells were added to an OP9-DL1 co-culture system, as shown in FIG. 8A. On day 41, the resulting cells were subjected to FACS analysis. As shown in FIG. 8B, it was found that the CD34+CD43+ cells produced in hematopoietic spheroids, with or without added cytokines, can generate CD4+CD8+ cells (immature T cells) consistently. However, the EBs+ cytokines could not (FIG. 8B).

Example 3

This example demonstrates that hematopoietic spheroids cultured in bioreactors can produce CD34+CD43+ cells.

Hematopoietic spheroids were prepared from hiPSC-derived EBs as described in Example 1, and added to the ABLE Bioreactor Magnetic Stir System 3D magnetic stir (Reprocell, Beltsville, MD) and disposable bioreactor to allow for mass production (FIG. 9A, Day 2). Hematopoietic spheroids (2000-2400) were cultured in 30 mL of differentiation medium in the bioreactors. On day 13, HPC were harvested and subjected to FACS analysis. As shown in FIG. 9B, 5-7% of cells generated from the hematopoietic spheroids cultured in the bioreactors expressed CD34+CD43+.

As shown in FIGS. 15A-15D, the expansion and differentiation of iPSC in the spheroids were enhanced by the stirred-suspension bioreactors as compared to those that were cultured in the plates.

Example 4

This example demonstrates that HPC derived from hematopoietic spheroids cultured in bioreactors have the potential to differentiate into T cells.

Hematopoietic spheroids which were prepared from human iPSC-derived EBs were added to the ABLE Bioreactor Magnetic Stir System 3D magnetic stir and disposable bioreactor cups to allow for mass production, as described in Example 3. On day 13, about $2.0 \sim 3.0 \times 10^5$ CD34+CD43+ expressing HPCs were harvested from the bioreactors (FIG. 10A). These cells were seeded onto OP9-DL1 mouse stromal cells with T cell differentiation medium. After 3 days, the floating cells were harvested by gently pipetting and the cells were then added to a new OP9-DL1 dish with T cell differentiation medium. From about day 16 to day 30, floating cells were re-seeded onto a new OP9-DL1 dish with T cell differentiation medium every 7 days. After day 30, floating cells were passaged onto a new OP9-DLL dish every 5 days. Using this process, the CD34+CD43+ HPCs can be differentiated to any one or more of CD4+, CD8+, CD3+, and/or CD7+ T cell lineage cells by approximately day 41 (FIG. 10A). The FACS analysis revealed that $2.0 \sim 3.0 \times 10^5$ expressed CD4+ and CD8+ on day 41. At around day 41, the CD4+CD8+ cells start to express CD3+, which is required for mature T cell activation (FIG. 10C). This shows that CD34+CD43+ cells produced in hematopoietic spheroids cultured in bioreactors can also differentiate to T cell lineage. As shown in FIG. 10B, 51.3% of cells derived from the hematopoietic spheroids cultured in bioreactors were CD4+CD8+, and 34.8% of those cells also expressed CD3+ on day 41 (FIG. 10C).

Example 5

This example demonstrates that human platelet lysate can be used for culturing hematopoietic spheroids in place of FCS control media.

In order to find a xeno-free medium for clinical applications of embodiments of the invention (without FCS), hematopoietic spheroids were cultured in XVIVO 10, XVIVO 15, XVIVO 20 (Lonza), and STEMPRO 34 (Thermo Fisher Scientific) xeno-free media for hematopoietic cells. Cells from hematopoietic spheroids cultured in this media were subjected to FACS analysis. The results are provided in FIGS. 11A-11B. As shown in FIGS. 11A and 11B, hematopoietic spheroids cultured in the control FCS media produced 5.86 CD34+CD43+ cells. Hematopoietic spheroids cultured in XVIVO 10 media produced 0.010 CD34+CD43+ cells. Hematopoietic spheroids cultured in XVIVO 15 media produced 0 CD34+CD43+ cells. Hematopoietic spheroids cultured in XVIVO 20 media produced very few CD34+CD43+ cells. In a second experiment, hematopoietic spheroids cultured in the control FCS media produced 0.31 CD34+CD43+ cells and hematopoietic spheroids cultured in STEMPRO 34 produced 0.019 CD34+CD43+ cells. As described above and shown in FIGS. 11A-11B, the xeno-free media tested were less effective in producing CD34+CD43+ cells than the FCS-containing control media (αMEM contained 20% FCS).

Next, xeno-free media for culturing hMSC was tested. However, as shown in FIG. 12, none of the tested media (MESENCULT (Stemcell Technologies), STEMPRO-MSC (Thermo Fisher Scientific), and human MESENCHYMAL-XF) performed as well as the FCS-containing control media. Specifically, hematopoietic spheroids cultured in the control FCS media produced 1.84 CD34+CD43+ cells. Hematopoietic spheroids cultured in MESENCULT produced 0.019 CD34+CD43+ cells. Hematopoietic spheroids cultured in STEMPRO-MSC produced 0.13 CD34+CD43+ cells. Hematopoietic spheroids cultured in Human Mesenchymal-XF produced very few CD34+CD43+ cells.

Next, αMEM containing 5% human platelet lysate (hPL) in place of the control media was tested (FIGS. 13A-13B), which was successful, as described below.

Hematopoietic spheroids which were prepared from hiPSC-derived EBs were added to the ABLE Bioreactor Magnetic Stir System 3D magnetic stir and disposable bioreactors to allow for mass production, as described in Example 3. Two bioreactors included αMEM 20% FCS as the control media. In two additional bioreactors, αMEM containing 5% hPL was used in place of the control media. As shown in FIGS. 13A-13B, cells from hematopoietic spheroids cultured in αMEM containing 5% hPL were subjected to FACS on days 13 and 36. FACS analysis revealed that HPC derived from hematopoietic spheroids cultured in αMEM containing 5% hPL produced CD34+CD43+ expressing cells on day 13 (FIG. 13A), and CD4+CD8+ expressing cells on day 36 (FIG. 13B). This confirmed that HPC derived from hematopoietic spheroids cultured in αMEM containing 5% hPL media can produce T cell lineage cells (CD4+CD8+).

αMEM containing 10% human platelet lysate (hPL) was also tested and it was found that αMEM containing 5% hPL media produces more HPC from iPSC.

Example 6

This example demonstrates that human iPSC can be scaled up and expanded in bioreactors.

The protocol described in Example 1 was modified for large-scale production and clinical application, as described below. A single cell suspension from undifferentiated human iPSC cultured on MATRIGEL membrane matrix coated dishes in ESSENTIAL 8 xeno-free media was prepared ($0.8 \times 10^5$ cells/mL). The adherent undifferentiated human iPSC were collected and transferred to bioreactors with ESSENTIAL 8 xeno-free media. Human MSC were added directly to the bioreactors. It was discovered that undifferentiated human iPSC can be expanded directly in bioreactors, and the iPSCs spontaneously form spheroids when they are cultured in suspension culture. Thus, undifferentiated spheroid-iPSC were collected in bioreactors with E8 xeno-free media and mixed with human MSC to make hematopoietic spheroids in directly in AGGREWELL 800 plates. This method simplifies the protocol by skipping the step of first making EBs in AGGREWELL 400 plates. As shown in FIG. 14, flow cytometric analysis of cells from spheroids cultured directly in bioreactors shows that at day 13, 3.69% of cells expressed CD34+CD43+. This result shows that this is a functional strategy to obtain CD34+CD43+ cells from human iPSC.

Example 7

This example demonstrates that HPC derived from hematopoietic spheroids cultured in bioreactors have the potential to differentiate into myeloid lineage cells.

CD34+CD43+ cells were collected from hematopoietic spheroids and cultured in methylcellulose based semi-solid media (FIG. 16A). After 14 days, colonies of myeloid lineage cells developed. The quantity of cell forming units (CFU) can be seen in FIG. 16B and include burst CFU erythoid, CFU macrophage, CFU granulocyte, and CFU macrophage and granulocyte.

Example 8

This example demonstrates that hematopoietic spheroids include iPSC and hMSC after several days of culturing.

GFP+ iPSC cells were used to detect if iPSC and hMSC (GFP−) cells were present in the hematopoietic spheroids. As seen in FIG. 17A, the number of hMSC reduced in number during culturing but iPSC were still at a higher number (as compared to hMSC) after day 4. FIG. 17B shows iPSC at day 8.

Although hMSC in the spheroids will reduce in number, iPSC-derived CD44+ or CD73+ cells from day 1 can be detected (FIG. 18). This indicates that iPSC began to generate mesenchymal lineage cells after contacting with hMSC (CD44 and CD73 are markers expressed in stomal cells including hMSC). The iPSC differentiated into primitive mesoderm stage (FIG. 19) and to hemogenic endothelium stage (FIG. 20) (even without addition of cytokines and growth factors).

Example 9

This example demonstrates that iPSC derived mesenchymal cells (iMC) can be used for co-culturing with iPSC (instead of hMSC).

Mesenchymal cells were obtained from iPSC. Briefly, NL5-GFP was added to iMC from NL5 or hMSC to form spheroids (FIG. 21, and see Takebe et al., *Cell Rep.*, 21(10): 2661-2670 (2017)). These spheroids were cultured in a stirred bioreactor to form HPC.

During the differentiation, iPSC began to downregulate Tra-1-60 expression (human embryonic stem cell marker) and upregulate the level of hMSC cell markers (e.g., PDGFRalpha, CD44, CD73, and CD105) (FIG. 22). FIGS. 23A-23B illustrate the results obtained when iMC was generated from NL5 iPSC and co-cultured with NL5-GFP iPSC. Also, iMC derived from D8, D14, and D20 was co-cultured with iPSC for HPC generation. iMC appeared to reduce in number (similar to the behavior of hMSC), however, iPSC still differentiated to HPC.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of preparing human CD34+CD43+ hematopoietic progenitor cells (HPC) in vitro, the method comprising:
   (i) culturing human source cells in a vessel;
   (ii) collecting the source cells from the vessel and preparing a single cell suspension of source cells;
   (iii) culturing the single cell suspension in a first three-dimensional (3D) culture and forming embryoid bodies (EBs) from the source cells in the first 3D culture;
   (iv) collecting the EBs, mixing the EBs with a single cell suspension of human mesoderm lineage cells (MLC), and preparing a suspension comprising EBs and MLC;
   (v) differentiating the EBs towards the mesoderm lineage by co-culturing the EBs and MLC in the suspension in a second 3D culture in the absence of exogenous cytokines and forming hematopoietic spheroids in the second 3D culture;
   (vi) collecting the hematopoietic spheroids from the second 3D culture and culturing the hematopoietic spheroids in a third 3D culture; and
   (vii) harvesting CD34+CD43+ hematopoietic progenitor cells from the hematopoietic spheroids.

2. The method of claim 1, wherein one or more of the first, second, and third 3D cultures is a hanging drop 3D culture, a 3D microwell culture, a 3D culture on a hydrophobic surface, a rotational culture, or a static 3D suspension culture.

3. The method of claim 1, wherein one or more of the first, second, and third 3D cultures is in a bioreactor.

4. The method of claim 1, wherein (vi) comprises culturing the hematopoietic spheroids in xeno-free medium.

5. The method of claim 4, wherein the xeno-free medium comprises human platelet lysate.

6. The method of claim 1, wherein any one or more of (i)-(iv) and (vi)-(vii) is carried out in the absence of one or more exogenous cytokines.

7. The method of claim 1, wherein any one or more of (i)-(iv) and (vi)-(vii) is carried out in the presence of one or more exogenous cytokines.

8. The method of claim 7, wherein the one or more exogenous cytokines comprise one or more of Fms-related tyrosine Kinase 3 (FLT3L), thrombopoietin (TPO), vascular endothelial growth factor (VEGF), platelet-derived growth factor (PDGF), fibroblast growth factor basic (bFGF), bone morphogenic protein 4 (BMP4), interleukin-3 (IL-3), interleukin-6 (IL-6), stem cell factor (SCF), granulocyte-colony stimulating factor (G-CSF), granulocyte macrophage-colony stimulating factor (GM-CSF), macrophage-colony stimulating factor (M-CSF), interferon alpha (IFNα), interferon beta (IFNβ), interferon gamma (IFNγ), tumor necrosis factor alpha (TNFα), tumor necrosis factor beta (TNFβ), WNT pathway activator CHIR99021, ascorbic acid, and mono-thioglycerol.

9. The method of claim 1, wherein (iii) further comprises reaggregating the single cell suspension by microcentrifugation.

10. The method of claim 1, wherein (i) comprises culturing the source cells in xeno-free medium.

11. The method of claim 1, wherein the source cells are induced pluripotent stem cells (iPSC), and the method further comprises reprogramming human T-cells to produce the iPSC.

12. The method of claim 1, wherein the source cells are induced pluripotent stem cells (iPSC), human embryonic stem cells (hESC), nuclear transfer-derived human embryonic stem cells, extended pluripotent stem cells (EPS), lineage-reprogrammed cells, transdifferentiated cells, dedifferentiated cells, or transdetermined cells.

13. The method of claim 1, further comprising differentiating the CD34+CD43+ hematopoietic progenitor cells to CD4+CD8+ cells.

* * * * *